United States Patent
Grandhe et al.

(10) Patent No.: US 9,959,388 B2
(45) Date of Patent: May 1, 2018

(54) SYSTEMS, DEVICES, AND METHODS FOR PROVIDING ELECTRICAL STIMULATION THERAPY FEEDBACK

(71) Applicant: BOSTON SCIENTIFIC NEUROMODULATION CORPORATION, Valencia, CA (US)

(72) Inventors: Sarvani Grandhe, Valencia, CA (US); Sridhar Kothandaraman, Valencia, CA (US); Soroush Massoumi, Los Angeles, CA (US); Rafael Carbunaru, Valley Village, CA (US); Dennis Zottola, Ventura, CA (US); Bradley Lawrence Hershey, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days. days.

(21) Appl. No.: 15/004,778

(22) Filed: Jan. 22, 2016

(65) Prior Publication Data
US 2016/0136443 A1    May 19, 2016

Related U.S. Application Data

(63) Continuation-in-part of application No. 14/807,466, filed on Jul. 23, 2015.
(Continued)

(51) Int. Cl.
*A61N 1/05* (2006.01)
*A61N 1/08* (2006.01)
(Continued)

(52) U.S. Cl.
CPC ..... *G06F 19/3418* (2013.01); *A61N 1/36071* (2013.01); *A61N 1/36132* (2013.01);
(Continued)

(58) Field of Classification Search
CPC .......................................................... A61N 1/05
(Continued)

(56) References Cited

U.S. PATENT DOCUMENTS

| | | | |
|---|---|---|---|
| 3,999,555 | A | 12/1976 | Person |
| 4,144,889 | A | 3/1979 | Tyers et al. |

(Continued)

FOREIGN PATENT DOCUMENTS

| | | |
|---|---|---|
| EP | 1048320 | 11/2000 |
| EP | 1166819 | 1/2002 |

(Continued)

OTHER PUBLICATIONS

Nowinski, W. L., et al., "Statistical analysis of 168 bilateral subthalamic nucleus implantations by means of the probabilistic functional atlas.", Neurosurgery 57(4 Suppl) (Oct. 2005).319-30.
(Continued)

*Primary Examiner* — Carl H Layno
*Assistant Examiner* — Jon Eric C Morales
(74) *Attorney, Agent, or Firm* — Lowe Graham Jones PLLC; Bruce E. Black

(57) ABSTRACT

A system for storing stimulation programs or sets of stimulation parameters includes at least one memory; at least one of i) multiple stimulation programs or ii) a multiple sets of stimulation parameters stored on the at least one memory from multiple different devices remote from the system and used to stimulate different patients; at least one processor coupled to the at least one memory to retrieve the stored stimulation programs or sets of stimulation parameters from the at least one memory when requested and to store additional stimulation programs or sets of stimulation parameters on the at least one memory; and a communications arrangement coupled to the at least one processor to deliver the stored stimulation programs or sets of stimulation
(Continued)

parameters to external device and to receive additional stimulation programs and sets of stimulation parameters from external devices.

17 Claims, 11 Drawing Sheets

Related U.S. Application Data

(60) Provisional application No. 62/028,704, filed on Jul. 24, 2014.

(51) Int. Cl.
  *G06F 19/00* (2018.01)
  *A61N 1/36* (2006.01)
  *A61N 1/372* (2006.01)

(52) U.S. Cl.
  CPC ..... *A61N 1/37235* (2013.01); *G06F 19/3406* (2013.01); *G06F 19/3481* (2013.01); *A61N 1/36125* (2013.01)

(58) Field of Classification Search
  USPC .................................................. 607/45, 59
  See application file for complete search history.

(56) References Cited

U.S. PATENT DOCUMENTS

| | | |
|---|---|---|
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulman |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillon et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |

(56) References Cited

U.S. PATENT DOCUMENTS

| | | |
|---|---|---|
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,136,518 B2 | 5/2006 | Griffin et al. |
| 7,058,446 B2 | 6/2006 | Schuler et al. |
| 7,082,333 B1 | 7/2006 | Bauhahn et al. |
| 7,107,102 B2 | 9/2006 | Daignault et al. |
| 7,126,000 B2 | 10/2006 | Ogawa et al. |
| 7,127,297 B2 | 10/2006 | Law et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst |
| 7,155,279 B2 | 12/2006 | Whitehurst |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | Dilorenzo |
| 7,211,050 B1 | 5/2007 | Caplygin |
| 7,216,000 B2 | 5/2007 | Sieracki et al. |
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,382 B2 | 3/2008 | McIntyre et al. |
| 7,388,974 B2 | 6/2008 | Yanagita |
| 7,437,193 B2 | 10/2008 | Parramon et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,019,439 B2 | 9/2011 | Kuzma et al. |
| 8,175,710 B2 | 5/2012 | He |
| 8,180,601 B2 | 5/2012 | Butson et al. |
| 8,195,300 B2 | 6/2012 | Gliner et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,364,278 B2 | 1/2013 | Pianca et al. |
| 8,429,174 B2 | 4/2013 | Ramani et al. |
| 8,452,415 B2 | 5/2013 | Goetz et al. |
| 8,543,189 B2 | 9/2013 | Paitel et al. |
| 8,606,360 B2 | 12/2013 | Butson et al. |
| 8,620,452 B2 | 12/2013 | King et al. |
| 8,918,184 B1 | 12/2014 | Torgerson et al. |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezei |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |
| 2007/0027514 A1 | 2/2007 | Gerber |
| 2007/0043268 A1 | 2/2007 | Russell |

(56) References Cited

U.S. PATENT DOCUMENTS

| | | |
|---|---|---|
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215101 A1 | 9/2008 | Rezai et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0163975 A1 | 6/2009 | Gerber et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0057161 A1 | 3/2010 | Machado et al. |
| 2010/0064249 A1 | 3/2010 | Groetken |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0324410 A1 | 12/2010 | Paek et al. |
| 2010/0331883 A1 | 12/2010 | Schmitz et al. |
| 2011/0040351 A1 | 2/2011 | Buston et al. |
| 2011/0066407 A1 | 3/2011 | Butson et al. |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0224665 A1 | 9/2011 | Crosby et al. |
| 2011/0251583 A1 | 10/2011 | Miyazawa et al. |
| 2011/0270348 A1 | 11/2011 | Goetz |
| 2011/0306845 A1 | 12/2011 | Osorio |
| 2011/0306846 A1 | 12/2011 | Osorio |
| 2011/0307032 A1 | 12/2011 | Goetz et al. |
| 2012/0027272 A1 | 2/2012 | Akinyemi et al. |
| 2012/0046715 A1 | 2/2012 | Moffitt et al. |
| 2012/0078106 A1 | 3/2012 | Dentinger et al. |
| 2012/0089205 A1 | 4/2012 | Boyden et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |
| 2012/0303098 A1 | 11/2012 | Perryman |
| 2012/0314924 A1 | 12/2012 | Carlton et al. |
| 2012/0316619 A1 | 12/2012 | Goetz et al. |
| 2013/0039550 A1 | 2/2013 | Blum et al. |
| 2013/0060305 A1 | 3/2013 | Bokil |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2014/0067018 A1 | 3/2014 | Carcieri et al. |
| 2014/0277284 A1 | 9/2014 | Chen et al. |
| 2015/0134031 A1 | 5/2015 | Moffitt et al. |

FOREIGN PATENT DOCUMENTS

| | | |
|---|---|---|
| EP | 1372780 | 1/2004 |
| EP | 1559369 | 8/2005 |
| WO | 97/39797 | 10/1997 |
| WO | 98/48880 | 11/1998 |
| WO | 01/90876 | 11/2001 |
| WO | 02/26314 | 4/2002 |

(56) References Cited

FOREIGN PATENT DOCUMENTS

| WO | 02/28473 | 4/2002 |
|---|---|---|
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 20071097859 | 8/2007 |
| WO | 20071097861 A1 | 8/2007 |
| WO | 2007/100427 | 9/2007 |
| WO | 2007/100428 | 9/2007 |
| WO | 2007/112061 | 10/2007 |
| WO | 2009097224 | 8/2009 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012088482 | 6/2012 |

OTHER PUBLICATIONS

Obeso, J. A., et al., "Deep-brain stimulation of the subthalamic nucleus or the pars interna of the globus pallidus in Parkinson's disease.", N Engl J Med., 345(13L. The Deep-Brain Stimulation for Parkinson's Disease Study Group, (Sep. 27, 2001 ),956-63.

Butson et al.. "Current Steering to control the vol. Of tissue activated during deep brain stimulation," vol. 1, No. 1, Dec. 3, 2007, pp. 7-15.

Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.

Phillips, M. D., et al., "Parkinson disease: pattern of functional MR imaging activation during deep brain stimulation of subthalamic nucleus—initial experience", Radiology 239(1), (Apr. 2006),209-16.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al., "Fast and robust multi-atlas segmentation of brain magnetic resonance images," NeuroImage, Academic Press, vol. 49, No. 3, Feb. 1, 2010, pp. 2352-2365.

McIntyre, C. C., et al., "How does deep brain stimulation work? Present understanding and future questions.", J Clin Neurophysiol. 21 (1 ). (Jan.-Feb. 2004 ),40-50.

Sanchez Castro et al., "A cross validation study of deep brain stimulation targeting: From experts to Atlas-Based, Segmentation-Based and Automatic Registration Algorithms." IEEE Transactions on Medical Imaging, vol. 25, No. 11, Nov. 1, 2006, pp. 1440-1450.

Plaha, P. , et al., "Stimulation of the caudal zona incerta is superior to stimulation of the subthalamic nucleus in improving contralateral parkinsonism.", Brain 129{Pt 7) (Jul. 2006), 1732-4 7.

Rattay, F, "Analysis of models for external stimulation of axons". IEEE Trans. Biomed. Eng. vol. 33 (1986),974-977.

Rattay, F., "Analysis of the electrical excitation of CNS neurons", IEEE Transactions on Biomedical Engineering 45 (6). (Jun. 1998),766-772.

Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.

Rubinstein, J. T., et al., "Signal coding in cochlear implants: exploiting stochastic effects of electrical stimulation", Ann Otol Rhinol Laryngol Suppl.. 191, (Sep. 2003), 14-9.

Schwan, H.P., et al., "The conductivity of living tissues.", Ann NY Acad Sci., 65(6). (AUQ., 1957),1007-13.

Taylor, R. S., et al., "Spinal cord stimulation for chronic back and leg pain and failed back surgery syndrome: a systematic review and analysis of prognostic factors", Spine 30(1 ). (Jan. 1, 2005), 152-60.

Siegel, Ralph M. et al., "Spatiotemporal dynamics of the functional architecture for gain fields in inferior parietal lobule of behaving monkey," Cerebral Cortex, New York, NY, vol. 17; No. 2, Feb. 2007, pp. 378-390.

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.

Geddes, L. A., et al.; "The specific resistance of biological material—a compendium of data for the biomedical engineer and physiologist.", Med Biol Ena. 5(3). (May 1967),271-93.

Gimsa, J., et al., "Choosing electrodes for deep brain stimulation experiments-electrochemical considerations.", J Neurosci Methods, 142(2), (Mar. 30, 2005),251-65.

Vidailhet, M. , et al., "Bilateral deep-brain stimulation of the globus pallidus in primary generalized dystonia", N Engl J Med. 352(5) (Feb. 3, 2005),459-67.

Izad, Oliver, "Computationally Efficient Method in Predicating Axonal Excitation," Dissertation for Master Degree, Department of Biomedical Engineering, Case Western Reserve University, May 2009.

Jaccard, Paul, "Elude comparative de la distribution florale dans une portion odes Aples et des Jura," Bulletin de la Societe Vaudoise des Sciences Naturelles (1901), 37:547-579.

Dice, Lee R., "Measures of the Amount of Ecologic Association Between Species," Ecology 26(3) (1945): 297-302. doi: 10.2307/1932409, http://jstor.org/stable/1932409.

Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.

Hubert, Lawrence et al., "Comparing partitions," Journal of Classification 2(1) (1985): 193-218, doi: 10.1007/BF01908075.

Cover, T.M. et al., "Elements of information theory," (1991) John Wiley & Sons, New York, NY.

Meila, Marina, "Comparing Clusterings by the Variation of Information," Learning Theory and Kernel Machines (2003): 173-187.

Viola, P., et al., "Alignment by maximization of mutual information", International Journal of Com outer Vision 24(2). ( 1997), 137-154.

Butson et al. "StimExplorer: Deep Brain Stimulation Parameter Selection Software System," Acta Neurochirugica, Jan. 1, 2007, vol. 97, No. 2, pp. 569-574.

Butson et al. "Role of Electrode Design on the Volume of Tissue Activated During Deep Brain Stimulation," Journal of Neural Engineering, Mar. 1, 2006, vol. 3, No. 1, pp. 1-8.

Volkmann et al., Indroduction to the Programming of Deep Brain Stimulators, Movement Disorders, vol. 17, Suppl. 3, pp. S181-S187 (2002).

Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.

Schmidt et al. "Sketching and Composing Widgets for 3D Manipulation," Eurographics, Apr. 2008, vol. 27. No. 2, pp. 301-310.

Volkmann, J. et al., "Basic algorithms for the programming of deep brain stimulation in Parkinson's disease". Mov Disord., 21 Suppl 14. (Jun. 2006),S284-9.

(56) References Cited

OTHER PUBLICATIONS

Walter, B. L., et al., "Surgical treatment for Parkinson's disease", Lancet Neural. 3(12). (Dec. 2004),719-28.
Wei, X. F., et al., "Current density distributions, field distributions and impedance analysis of segmented deep brain stimulation electrodes", J Neural Eng .. 2(4). (Dec. 2005), 139-47.
Zonenshayn, M. , et al., "Location of the active contact within the subthalamic nucleus (STN) in the treatment of idiopathic Parkinson's disease.", Surg Neurol., 62(3) (Sep. 2004),216-25.
Da Silva et al (A primer on diffusion tensor imaging of anatomical substructures. Neurosurg Focus 15(1): p. 1-4, Article 4, 2003.)
Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.
Grill, W. M., "Stimulus waveforms for selective neural stimulation", IEEE Engineering in Medicine and Biology Magazine, 14(4}, (Jul.-Aug. 1995), 375-385.
Miocinovic, S., et al., "Sensitivity of temporal excitation properties to the neuronal element activated by extracellular stimulation", J Neurosci Methods. 132(1). (Jan. 15, 2004), 91-9.
Hunka, K. et al., Nursing Time to Program and Assess Deep Brain Stimulators in Movement Disorder Patients, J. Neursci Nurs., 37: 204-10 (Aug. 2005).
Moss, J. , et al., "Electron microscopy of tissue adherent to explanted electrodes in dystonia and Parkinson's disease", Brain, 127{Pt 12). (Dec. 2004 ),2755-63.
Montgomery, E. B., et al., "Mechanisms of deep brain stimulation and future technical developments.", Neurol Res. 22(3). (Apr. 2000),259-66.
Merrill, D. R., et al., "Electrical stimulation of excitable tissue design of efficacious and safe protocols". J Neurosci Methods. 141(2). (Feb. 15, 2005), 171-98.
Fisekovic et al., "New Controller for Functional Electrical Stimulation Systems", Med. Eng. Phys. 2001; 23:391-399.
Zhang, Y., et al., "Atlas-guided tract reconstruction for automated and comprehensive examination of the white matter anatomy," Neuroimage 52(4) (2010), pp. 1289-1301.
""BioPSE" The Biomedical Problem Solving Environment", htt12://www.sci.utah.edu/cibc/software/index.html, MCRR Center for Integrative Biomedical Computing,(2004).
Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003),1-13.
Carnevale, N.T. et al., "The Neuron Book," Cambridge. UK: Cambridge University Press (2006), 480 pages.
Chaturvedi: "Development of Accurate Computational Models for Patient-Specific Deep Brain Stimulation," Electronic Thesis or Dissertation, Jan. 2012, 162 pages.
Chaturvedi, A. et al.: "Patient-specific models of deep brain stimulation: Influence of field model complexity on neural activation predictions." Brain Stimulation, Elsevier, Amsterdam, NL, vol. 3, No. 2 Apr. 2010, pp. 65-77.
Frankemolle, et al., "Reversing cognitive-motor impairments in Parkinson's disease patients using a computational modeling approach to deep brain stimulation programming," Brian 133 (2010), pp. 746-761.
McIntyre, C.C., et al., "Modeling the excitablitity of mammalian nerve fibers: influence of afterpotentials on the recovery cycle," J Neurophysiol, 87(2) (Feb. 2002), pp. 995-1006.
Peterson, et al., "Predicting myelinated axon activation using spatial characteristics of the extracellular field," Journal of Neural Engineering, 8 (2011), 12 pages.
Warman, et al., "Modeling the Effects of Electric Fields on nerver Fibers; Dermination of Excitation Thresholds,"IEEE Transactions on Biomedical Engineering, vol. 39, No. 12 (Dec. 1992), pp. 1244-1254.

Wesselink, et al., "Analysis of Current Density and Related Parameters in Spinal Cord Stimulation," IEEE Transactions on Rehabilitation Engineering, vol. 6, No. 2 Jun. 1998, pp. 200-207.
Andrews, R. J., "Neuroprotection trek—the next generation: neuromodulation II. Applications—epilepsy, nerve regeneration, neurotrophins.", Ann NY Acad Sci. 993 (May 2003), 14-24.
Astrom, M. , et al., "The effect of cystic cavities on deep brain stimulation in the basal ganglia: a simulation-based study", J Neural Eng., 3(2), (Jun. 2006).132-8.
Bazin et al., "Free Software Tools for Atlas-based Volumetric Neuroimage Analysis", Proc. SPIE 5747, Medical Imaging 2005: Image Processing, 1824 May 5, 2005.
Back, C. , et al., "Postoperative Monitoring of the Electrical Properties of Tissue and Electrodes in Deep Brain Stimulation", Neuromodulation, 6(4), (Oct. 2003 ),248-253.
Baker, K. B., et al., "Evaluation of specific absorption rate as a dosimeter of MRI-related implant heating", J Magn Reson Imaging., 20(2), (Aug. 2004),315-20.
Brown, J. "Motor Cortex Stimulation," Neurosurgical Focus ( Sep. 15, 2001) 11(3):E5.
Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.
Cesselin, F. "Opioid and anti-opioid peptides," Fundamental and Clinical Pharmacology (1995) 9(5): 409-33 (Abstract only).
Rezai et al., "Deep Brain Stimulation for Chronic Pain" Surgical Management of Pain, Chapter 44 pp. 565-576 (2002).
Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.
Bedard, C. , et al., "Modeling extracellular field potentials and the frequency-filtering properties of extracellular space", Biophys J .. 86(3). (Mar. 2004),1829-42.
Benabid, A. L., et al., "Future prospects of brain stimulation", Neurol Res.;22(3), (Apr. 2000),237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.
Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005),196-197.
Mcintyre, Cameron C., et al., "Cellular effects of deep brain stimulation model-based analysis of activation and inhibition," J Neurophysiol, 91(4) (Apr. 2004), pp. 1457-1469.
Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assisted Intervention-Mic CAI 2006 Lecture Notes in Computer Science; LNCS, Springer, Berlin, DE.
Butson, C. R., et al., "Deep brainstimulation interactive visualization system", Society for Neuroscience vol. 898.7 (2005).
Hodaie, M., et al., "Chronic anterior thalamus stimulation for intractable epilepsy," Epilepsia, 43(6) (Jun. 2002), pp. 603-608.
Hoekema, R., et al., "Multigrid solution of the potential field in modeling electrical nerve stimulation," Comput Biomed Res., 31(5) (Oct. 1998), pp. 348-362.
Holsheimer, J., et al., "Identification of the target neuronal elements in electrical deep brain stimulation," Eur J Neurosci., 12(12) (Dec. 2000), pp. 4573-4577.
Jezernik, S., et al., "Neural network classification of nerve activity recorded in a mixed nerve," Neurol Res., 23(5) (Jul. 2001), pp. 429-434.

(56) References Cited

OTHER PUBLICATIONS

Jones, DK., et al., "Optimal strategies for measuring diffusion in anisotropic systems by magnetic resonance imaging," Magn. Reson. Med., 42(3) (Sep. 1999), pp. 515-525.
Krack, P., et al., "Postoperative management of subthalamic nucleus stimulation for Parkinson's disease," Mov. Disord., vol. 17(suppl 3) (2002), pp. 188-197.
Le Bihan, D., et al.. "Diffusion tensor imaging: concepts and applications," J Magn Reson Imaging. 13(4) (Apr. 2001), pp. 534-546.
Lee, D. C., et al., "Extracellular electrical stimulation of central neurons: quantitative studies." In: Handbook of neuroprosthetic methods. WE Finn and PG Lopresti (eds) CRC Press (2003), pp. 95-125.
Levy, AL., et al., "An Internet-connected, patient-specific, deformable brain atlas integrated into a surgical navigation system," J Digit Imaging, 10(3 Suppl 1) (Aug. 1997), pp. 231-237.
Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.
Mcintyre, C. C., et al., "Extracellular stimulation of central neurons: influence of stimulus waveform and frequency on neuronal output," J. Neurophysiol., 88(4), (Oct. 2002), pp. 1592-1604.
Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.
Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.
Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.
Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.
Mcintyre, Cameron C., et al., "Modeling the excitability of mammalian nerve fibers: influence of aflerpotentials on the recovery cycle," J Neurophysiol, 87(2) (Feb. 2002), pp. 995-1006.
Mcintyre, Cameron C., el al., "Selective microstimulation of central nervous system neurons," Annals of biomedical engineering, 28(3) (Mar. 2000), pp. 219-233.
Mcintyre, C. C., et al., "Sensitivity analysis of a model of mammalian neural membrane," Biol Cybern.. 79(1) (Jul. 1998), pp. 29-37.
Mcintyre, Cameron C., et al., "Uncovering the mechanism(s) of action of deep brain stimulation: activation, inhibition, or both," Clin Neurophysiol, 115(6) (Jun. 2004), pp. 1239-1248.
Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.
Mouine et al. "Multi-Strategy and Multi-Algorithm Cochlear Prostheses", Biomed. Sci. Instrument, 2000; 36:233-238.
Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.
Mcintyre, Cameron C., et al., "Electric field generated by deep brain stimulation of the subthalamic nucleus," Biomedical Engineering Society Annual Meeting, Nashville TN (Oct. 2003), 16 pages.
Mcintyre, Cameron C., et al., "Excitation of central nervous system neurons by nonuniform electric fields," Biophys. J., 76(2) (1999), pp. 878-888.
McNeal, DR., et al., "Analysis of a model for excitation of myelinated nerve," IEEE Trans Biomed Eng., vol. 23 (1976), pp. 329-337.
Micheli-Tzanakou, E., et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.
Miocinovic, S., et al., "Computational analysis of subthalamic nucleus and lenticular fasciculus activation during therapeutic deep brain stimulation," J Neurophysiol., 96(3) (Sep. 2006), pp. 1569-1580.
Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.
Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Enginering, 50(9) (Sep. 2003), pp. 1074-1085.
Moffitt, MA., et al., "Prediction of myelinated nerve fiber stimulation thresholds: limitations of linear models." IEEE Transactions on Biomedical Engineering, 51 (2) (2003). pp. 229-236.
Moro, E, et al., "The impact on Parkinson's disease of electrical parameter settings in STN stimulation." Neurology, 59 (5) (Sep. 10, 2002), pp. 706-713.
Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.
Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.
O'Suilleabhain, PE., et al., "Tremor response to polarity, voltage, pulsewidth and frequency of thalamic stimulation," Neurology, 60(5) (Mar. 11, 2003), pp. 786-790.
Pierpaoli, C., et al., "Toward a quantitative assessment of diffusion anisotropy," Magn Reson Med., 36(6) (Dec. 1996), pp. 893-906.
Plonsey, R., et al., "Considerations of quasi-stationarity in electrophysiological systems," Bull Math Biophys., 29(4) (Dec. 1967), pp. 657-664.
Ranck, J B., "Specific impedance of rabbit cerebral cortex," Exp. Neurol., vol. 7 (Feb. 1963), pp. 144-152.
Ranck, J B., et al., "The Specific impedance of the dorsal columns of the cat: an anisotropic medium," Exp. Neurol., 11 (Apr. 1965), pp. 451-463.
Ranck, J B., "Which elements are excited in electrical stimulation of mammalian central nervous system: a review," Brain Res., 98(3) (Nov. 21, 1975). pp. 417-440.
Rattay, F., et al., "A model of the electrically excited human cochlear neuron. I. Contribution of neural substructures to the generation and propagation of spikes," Hear Res., 153(1-2) (Mar. 2001), pp. 43-63.
Rattay, F., "A model of the electrically excited human cochlear neuron. II. Influence of the three-dimensional cochlear structure on neural excitability," Hear Res., 153(1-2) (Mar. 2001), pp. 64-79.
Rattay, F., "Arrival at Functional Electrostimulation by modelling of fiber excitation," Proceedings of the Ninth annual Conference of the IEEE Engineering in Medicine and Biology Society (1987), pp. 1459-1460.
Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.
Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.

(56) References Cited

OTHER PUBLICATIONS

Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.

Sances, A., et al., "In Electroanesthesia: Biomedical and Biophysical Studies," A Sances and SJ Larson, Eds., Academic Press, NY (1975), pp. 114-124.

SI. Jean, P., et al., "Automated atlas integration and interactive three-dimensional visualization tools for planning and guidance in functional neurosurgery," IEEE Transactions on Medical Imaging, 17(5) (1998), pp. 672-680.

Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.

Steno, D., et al., "Neurophysiological refinement of subthalamic nucleus targeting," Neurosurgery, 50(1) (Jan. 2002), pp. 58-69.

Struijk, J. J., et al., "Excitation of dorsal root fibers in spinal cord stimulation: a theoretical study," IEEE Transactions on Biomedical Engineering, 40(7) (Jul. 1993), pp. 632-639.

Struijk, J J., et al., "Recruitment of dorsal column fibers in spinal cord stimulation: influence of collateral branching," IEEE Transactions on Biomedical Engineering, 39(9) (Sep. 1992), pp. 903-912.

Tamma, F., et al., "Anatomo-clinical correlation of intraoperative stimulation-induced side-effects during HF-DBS of the subthalamic nucleus." Neurol Sci., vol. 23 (Suppl 2) (2002), pp. 109-110.

Tarler, M., et al., "Comparison between monopolar and tripolar configurations in chronically implanted nerve cuff electrodes." IEEE 17th Annual Conference Engineering in Medicine and Biology Society, vol. 2 (1995), pp. 1093-1109.

Testerman, Roy L., "Coritical response to callosal stimulation: A model for determining safe and efficient stimulus parameters," Annals of Biomedical Engineering, 6(4) (1978), pp. 438-452.

Tuch, D.S., et al., "Conductivity mapping of biological tissue using diffusion MRI," Ann NY Acad Sci., 888 (Oct. 30, 1999), pp. 314-316.

Tuch, D.S., et al., "Conductivity tensor mapping of the human brain using diffusion tensor MRI," Proc Nall Acad Sci USA, 98(20) (Sep. 25, 2001), pp. 11697-11701.

Veraart, C., et al., "Selective control of muscle activation with a multipolar nerve cuff electrode," IEEE Transactions on Biomedical Engineering, 40(7) (Jul. 1993), pp. 640-653.

Vercueil, L., et al., "Deep brain stimulation in the treatment of severe dystonia," J. Neurol., 248(8) (Aug. 2001 ), pp. 695-700.

Vilalte, "Circuit Design of the Power-on-Reset," Apr. 2000, pp. 1-25.

Vitek, J. L., "Mechanisms of deep brain stimulation: excitation or inhibition," Mov. Disord., vol. 17 (Suppl. 3) (2002), pp. 69-72.

Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.

Wakana, S., et al.. "Fiber tract-based atlas of human white matter anatomy," Radiology, 230(1) (Jan. 2004). pp. 77-87.

Alexander, DC., et al., "Spatial transformations of diffusion tensor magnetic resonance images," IEEE Transactions on Medical Imaging, 20 (11), (2001), pp. 1131-1139.

Wu, Y. R., et al., "Does Stimulation of the GPi control dyskinesia by activating inhibitory axons?," Mov. Disord., vol. 16 (2001), pp. 208-216.

Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.

Yianni, John, et al., "Globus pallidus internus deep brain stimulation for dystonic conditions: a prospective audit," Mov. Disord., vol. 18 (2003), pp. 436-442.

Zonenshayn, M., et al., "Comparison of anatomic and neurophysiological methods for subthalamic nucleus targeting," Neurosurgery, 47(2) (Aug. 2000), pp. 282-294.

Voghell et al., "Programmable Current Source Dedicated to Implantable Microstimulators" ICM '98 Proceedings of the Tenth International Conference, pp. 67-70.

Butson, Christopher R., et al., "Patient-specific analysis of the volume of tissue activated during deep brain stimulation", NeuroImage. vol. 34. (2007),661-670.

Adler, DE., et al., "The tentorial notch: anatomical variation, morphometric analysis, and classification in 100 human autopsy cases," J. Neurosurg., 96(6), (Jun. 2002), pp. 1103-1112.

Jones et al., "An Advanced Demultiplexing System for Physiological Stimulation", IEEE Transactions on Biomedical Engineering, vol. 44 No. 12 Dec. 1997, pp. 1210-1220.

Alo, K. M., et al., "New trends in neuromodulation for the management of neuropathic pain," Neurosurgery, 50(4), (Apr. 2002), pp. 690-703, discussion pp. 703-704.

Ashby, P., et al., "Neurophysiological effects of stimulation through electrodes in the human subthalamic nucleus," Brain, 122 (PI 10), (Oct. 1999), pp. 1919-1931.

Baker, K. B., et al., "Subthalamic nucleus deep brain stimulus evoked potentials: Physiological and therapeutic implications," Movement Disorders, 17(5), (Sep./Oct. 2002), pp. 969-983.

Bammer, R, et al., "Diffusion tensor imaging using single-shot SENSE-EPI", Magn Reson Med., 48(1 ), (Jul. 2002), pp. 128-136.

Basser, PJ., et al., "MR diffusion tensor spectroscopy and imaging," Biophys J., 66(1 ), (Jan. 1994), pp. 259-267.

Basser, P J., et al.. "New currents in electrical stimulation of excitable tissues," Annu Rev Biomed Eng., 2, (2000). pp. 377-397.

Benabid, AL., et al., "Chronic electrical stimulation of the ventralis intermedius nucleus of the thalamus as a treatment of movement disorders," J. Neurosurg., 84(2), (Feb. 1996), pp. 203-214.

Benabid, AL., et al., "Combined (Ihalamotoy and stimulation) stereotactic surgery of the VIM thalamic nucleus for bilateral Parkinson disease," Appl Neurophysiol, vol. 50, (1987), pp. 344-346.

Benabid, A L., et al., "Long-term suppression of tremor by chronic stimulation of the ventral intermediate thalamic nucleus," Lancet. 337 (8738), (Feb. 16, 1991 ), pp. 403-406.

Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS). vol. 4191, pp. 429-437, LNCS, Springer, Berlin, DE.

Christensen, Gary E., et al., "Volumetric transformation of brain anatomy," IEEE Transactions on Medical Imaging, 16 (6), (Dec. 1997), pp. 864-877.

Cooper, S , et al., "Differential effects of thalamic stimulation parameters on tremor and paresthesias in essential tremor," Movement Disorders, 17(Supp. 5), (2002), p. S193.

Coubes, P, et al., "Treatment of DYT1-generalised dystonia by stimulation of the internal globus pallidus," Lancet. 355 (9222), (Jun. 24, 2000), pp. 2220-2221.

Dasilva, A.F. M., et al., "A Primer Diffusion Tensor Imaging of Anatomical Substructures," Neurosurg. Focus; 15(1) (Jul. 2003), pp. 1-4.

Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.

Finnis, K. W., et al., "3-D functional atlas of subcortical structures for image guided stereotactic neurosurgery," Neuroimage, vol. 9, No. 6, Iss. 2 (1999), p. S206.

Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference.Cambridge, UK, Sep. 19-22, 1999, Proceedings (1999), pp. 758-767.

Finnis, K. W., et al., "A 3-Dimensional Database of Deep Brain Functional Anatomy, and Its Application to Image-Guided Neurosurgery," Proceedings of the Third International Conference on

(56) References Cited

OTHER PUBLICATIONS

Medical Image Computing and Computer-Assisted Intervention. Lecture Notes in Computer Science: vol. 1935 (2000), pp. 1-8.
Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11. Lecture Notes In Computer Science; vol. 2489 (2002), pp. 69-76.
Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002). pp. 184-195.
Finnis, Krik W., et al., "Three-Dimensional Database of Subcortical Electrophysiology for Image-Guided Stereotatic Functional Neurosurgery," IEEE Transactions on Medical Imaging. 22(1) (Jan. 2003), pp. 93-104.
Gabriels, L, et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.
Goodall, E. V., et al., "Position-selective activation of peripheral nerve fibers with a cuff electrode," IEEE Transactions on Biomedical Engineering, 43(8) (Aug. 1996), pp. 851-856.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995), pp. 375-385.
Grill, W. M., et al., "Temporal stability of nerve cuff electrode recruitment properties," IEEE 17th Annual Conference Engineering in Medicine and Biology Society, vol. 2 (1995), pp. 1089-1090.

Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No tissue damage by chronic deep brain stimulation in Parkinson's disease," Ann Neurol 48(3) (Sep. 2000), pp. 372-376.
Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.
Haueisen, J , et al., "The influence of brain tissue anisotropy on human EEG and MEG," Neuroimage, 15(1) (Jan. 2002), pp. 159-166.
D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Dawant et al., Biomedical Image Registration. Lecture Notes in Computer Science, 2003, vol. 2717, 2003, 142-150.
Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.
Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.
Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based on Electrode Placement", Arch Neural., 65:612-616, May 2008.
Butson et al., "Tissue and Electrode Capacitance Reduce Neural Activation Volumes During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:44 7-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.

(56) References Cited

OTHER PUBLICATIONS

Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.
Machado et al., "Deep Brain Stimulation for Parkinson's Disease: Surgical Technique and Perioperative Management", Movement Disorders, 21 :S247-S258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision-Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural Neurosurg. Psychiatry, 76:1161-1163, Aug. 2005.
Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.
Ward, H. E et al., "Update on deep brain stimulation for neuropsychiatric disorders," Neurobiol Dis 38 (3) (2010), pp. 346-353.
Alberts et al. "Bilateral subthalamic stimulation impairs cognitive-motor performance in Parkinson's disease patients." Brain (2008), 131, 3348-3360, Abstract.
Butson, Christopher R., et al., "Sources and effects of electrode impedance during deep brain stimulation", Clinical Neurophysiology. vol. 117.(2006),447-454.
An. et al., "Prefronlal cortical projections to longitudinal columns in the midbrain periaqueductal gray in macaque monkeys," J Comp Neural 401 (4) (1998), pp. 455-479.
Bulson, C. R., et al., "Tissue and electrode capacitance reduce neural activation volumes during deep brain stimulation," Clinical Neurophysiology, vol. 116 (2005), pp. 2490-2500.
Carmichael, S. T.. et al., "Connectional networks within the orbital and medial prefronlal cortex of macaque monkeys," J Comp Neural 371 (2) (1996), pp. 179-207.
Croxson, et al., "Quantitative investigation of connections of the prefronlal cortex in the human and macaque using probabilistic diffusion tractography," J Neurosci 25 (39) (2005), pp. 8854-8866.
Frankemolle, et al., "Reversing cognitive-motor impairments in Parkinson's disease patients using a computational modelling approach to deep brain stimulation programming," Brain 133 (2010), pp. 746-761.
Freedman, et al., "Subcortical projections of area 25 (subgenual cortex) of the macaque monkey," J Comp Neurol 421 (2) (2000), pp. 172-188.
Giacobbe, et al., "Treatment resistant depression as a failure of brain homeostatic mechanisms: implications for deep brain stimulation," Exp Neural 219 (1) (2009), pp. 44-52.
Goodman, et al., "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: worldwide experience," Mol Psychiatry 15 (1) (2010), pp. 64-79.
Greenberg. et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.

Haber, et al., "Reward-related cortical inputs define a large striatal region in primates that interface with associative cortical connections, providing a substrate for incentive-based learning," J Neurosci 26 (32) (2006), pp. 8368-8376.
Haber, et al., "Cognitive and limbic circuits that are affected by deep brain stimulation," Front Biosci 14 (2009), pp. 1823-1834.
Hines, M. L., et al., "The Neuron simulation environment," Neural Comput., 9(6) (Aug. 15, 1997), pp. 1179-1209.
Hua, et al., "Tract probability maps in stereotaxic spaces: analyses of white matter anatomy and tract-specific quantification," Neuroimage 39 (1) (2008), pp. 336-347.
Johansen-Berg, et al., "Anatomical connectivity of the subgenual cingulate region targeted with deep brain stimulation for treatment-resistant depression," Cereb Cortex 18 (6) (2008), pp. 1374-1383.
Kopell, et al., "Deep brain stimulation for psychiatric disorders," J Clin Neurophysiol 21 (1) (2004), pp. 51-67.
Lozano, et al., "Subcallosal cingulate gyrus deep brain stimulation for treatment-resistant depression," Biol Psychiatry (6) (2008), pp. 461-467.
Lujan, et al., "Tracking the mechanisms of deep brain stimulation for neuropsychiatric disorders," Front Biosci 13 (2008), pp. 5892-5904.
Lujan, J.L. et al., "Automated 3-Dimensional Brain Atlas Fitting to Microelectrode Recordings from Deep Brain Stimulation Surgeries," Stereotact. Fune!. Neurosurg. 87(2009), pp. 229-240.
Machado. et al., "Functional topography of the ventral striatum and anterior limb of the internal capsule determined by electrical stimulation of awake patients," Clin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Mayberg, H. S., et al., "Deep brain stimulation for treatment-resistant depression," Neuron, 45(5) (Mar. 3, 2005), pp. 651-660.
Mayberg, H. S., et al., "Limbic-cortical dysregulation: a proposed model of depression," J Neuropsychiatry Clin Neurosci. 9 (3) (1997), pp. 471-481.
McIntyre,C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neurol 216 (i) (2009), pp. 166-176.
Nuttin, et al., "Electrical stimulation in anterior limbs of internal capsules in patients with obsessive-compulsive disorder," Lancet 354 (9189) (1999), p. 1526.
Saxena, et al., "Cerebral glucose metabolism in obsessive-compulsive hoarding," Am J Psychiatry. 161 (6) (2004), pp. 1038-1048.
Viola, et al., "Importance-driven focus of attention," IEEE Trans Vis Comput Graph 12 (5) (2006), pp. 933-940.
Wakana, S., et al., "Reproducibility of quantitative tractography methods applied to cerebral white matter," Neuroimage 36 (3) (2007), pp. 630-644.
Mayr et al., "Basic Design and Construction of the Vienna FES Implants: Existing Solutions and Prospects for New Generations of Implants", Medical Engineering & Physics, 2001: 23:53-60.
McIntyre, Cameron , et al., "Finite element analysis of the current-density and electric field generated by metal microelectrodes", Ann Biomed Eng . 29(3), (2001 ),227-235.
Foster, K. R., et al., "Dielectric properties of tissues and biological materials: a critical review.", Grit Rev Biomed Ena. 17(1 ). {1989),25-104.
Limousin, P., et al., "Electrical stimulation of the subthalamic nucleus in advanced Parkinson's disease", N Engl J Med .. 339(16), (Oct. 15, 1998), 1105-11.
Kitagawa, M., et al., "Two-year follow-up of chronic stimulation of the posterior subthalamic white matter for tremor-dominant Parkinson's disease.", Neurosurgery. 56(2). (Feb. 2005):281-9.
Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.

(56) References Cited

OTHER PUBLICATIONS

Holsheimer, J., et al., "Chronaxie calculated from current-duration and voltage-duration data", J Neurosci Methods. 97(1). (Apr. 1, 2000),45-50.
Hines, M. L., et al., "The Neuron simulation environment", Neural Comput. 9(6). (Aug. 15, 1997), 1179-209.
Herzog, J., et al., "Most effective stimulation site in subthalamic deep brain stimulation for Parkinson's disease", Mov Disord. 19(9). (Sep. 2004),1050-4.
Hershey, T., et al., "Cortical and subcortical blood flow effects of subthalamic nucleus stimulation in PD.", Neurology 61(6). (Sep. 23, 2003),816-21.
Hemm, S., et al., "Evolution of Brain Impedance in Dystonic Patients Treated by GPi Electrical Stimulation", Neuromodulation 7(2) (Apr. 2004),67-75.
Hemm, S., et al., "Deep brain stimulation in movement disorders: stereotactic coregistration of two-dimensional electrical field modeling and magnetic resonance imaging.", J Neurosurg. 103(6): (Dec. 2005),949-55.
Haueisen, J, et al., "The influence of brain tissue anisotropy on human EEG and MEG", Neuroimage 15(1) (Jan. 2002),159-166.
Haslinger, B., et al., "Frequency-correlated decreases of motor cortex activity associated with subthalamic nucleus stimulation in Parkinson's disease.", Neuroimage 28(3). (Nov. 15, 2005),598-606.
Hashimoto, T., et al., "Stimulation of the subthalamic nucleus changes the firing pattern of pallidal neurons", J Neurosci. 23(5). (Mar. 1, 2003),1916-23.
Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8. 2002),238-55.
McNaughtan et al., "Electrochemical Issues in Impedance Tomography", 1st World Congress on Industrial Process Tomography, Buxton, Greater Manchester, Apr. 14-17, 1999.
Grill, WM., et al "Electrical properties of implant encapsulation tissue", Ann Biomed Eng. vol. 22. (1994),23-33.
Grill, W. M., et al., "Deep brain stimulation creates an informational lesion of the stimulated nucleus", Neuroreport. 15I7t (May 19, 2004 ), 1137-40.
Official Communication from U.S. Appl. No. 14/881,466, dated Jun. 19, 2017, 15 pages.
Official Communication from U.S. Appl. No. 14/807,466, dated Jan. 3, 2017, 10 pages.

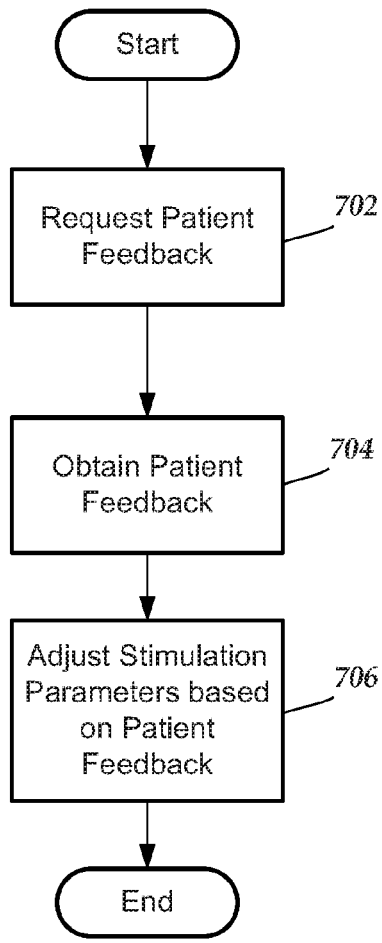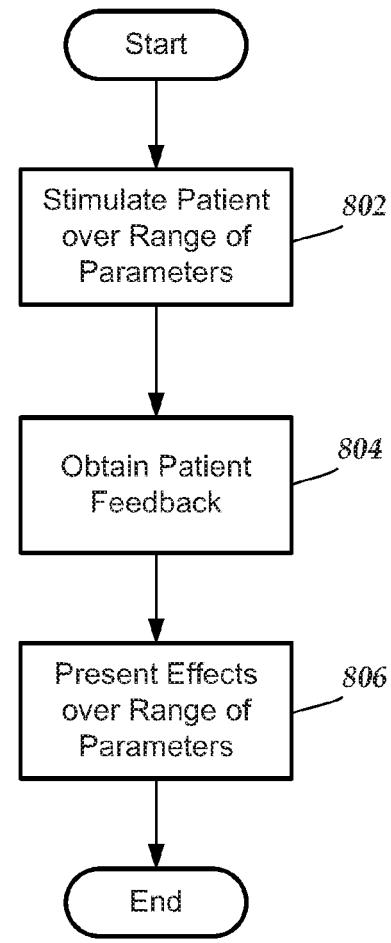
Fig. 7
Fig. 8

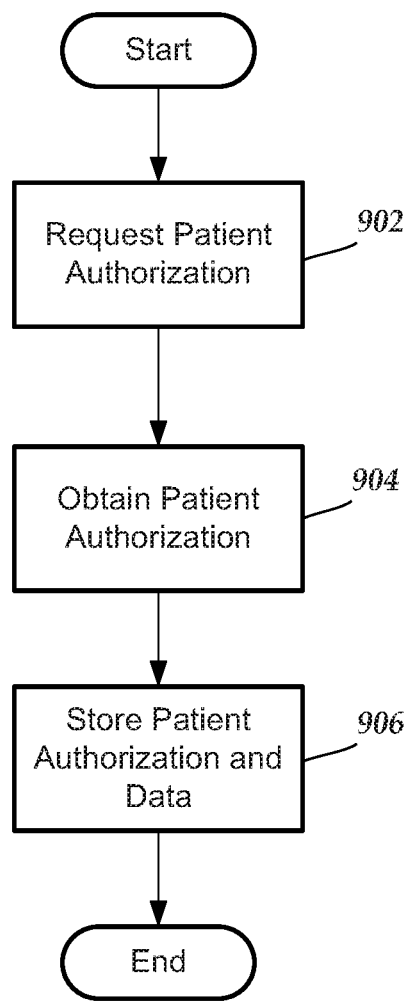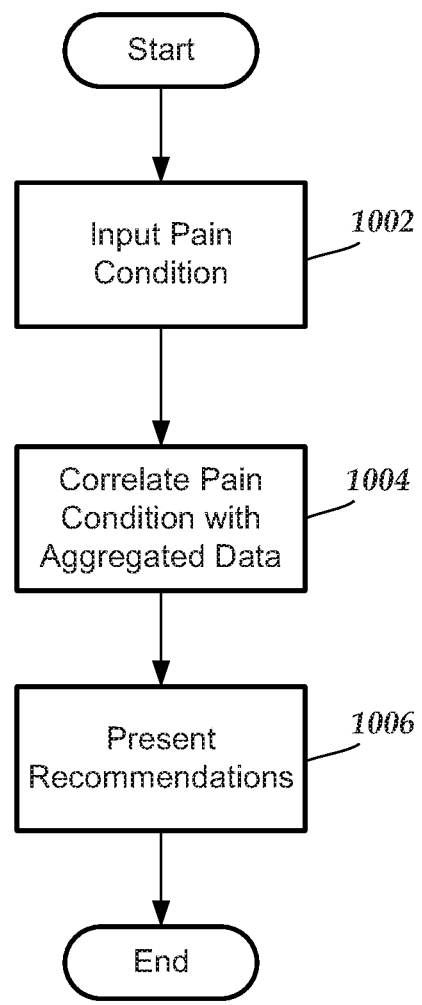
Fig. 9
Fig. 10

SYSTEMS, DEVICES, AND METHODS FOR PROVIDING ELECTRICAL STIMULATION THERAPY FEEDBACK

CROSS-REFERENCE TO RELATED APPLICATIONS

This application is a continuation-in-part of U.S. patent application Ser. No. 14/807,466 filed Jul. 23, 2015 which claims the benefit under 35 U.S.C. § 119(e) of U.S. Provisional Patent Application Ser. No. 62/028,704 filed Jul. 24, 2014, both of which are incorporated herein by reference in their entireties.

FIELD

The present invention is directed to the area of implantable electrical stimulation systems and methods of making and using the systems. The present invention is also directed to implantable electrical stimulation systems include devices or methods for providing feedback regarding electrical stimulation, as well as methods of making and using the electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include an implantable pulse generator (IPG), one or more leads, and an array of stimulator electrodes on each lead. The stimulator electrodes are in contact with or near the nerves, muscles, or other tissue to be stimulated. The pulse generator generates electrical pulses that are delivered by the electrodes to body tissue.

BRIEF SUMMARY

One embodiment is a system for storing stimulation programs or sets of stimulation parameters. The system includes at least one memory; at least one of i) a plurality of stimulation programs or ii) a plurality of sets of stimulation parameters stored on the at least one memory from a plurality of different devices remote from the system and used to stimulate a plurality of different patients; at least one processor coupled to the at least one memory to retrieve the stored stimulation programs or sets of stimulation parameters from the at least one memory when requested and to store additional stimulation programs or sets of stimulation parameters on the at least one memory; and a communications arrangement coupled to the at least one processor to deliver the stored stimulation programs or sets of stimulation parameters to external device and to receive additional stimulation programs and sets of stimulation parameters from external devices.

In at least some embodiments, the system further includes lead placement information for at least one stimulation therapy stored on the at least one memory and accessible via the at least one processor and communications arrangement.

In at least some embodiments, the system is configured and arranged, via the at least one processor and communications arrangement, to receive a score or rating for at least one of the stimulation programs or sets of stimulation parameters and to store, on the at least one memory, the score or rating in conjunction with that at least one of the stimulator programs or sets of stimulation parameters. In at least some embodiments, the system is configured and arranged, via the at least one processor and communications arrangement, to request the score or rating for at least one of the stimulation programs or sets of stimulation parameters from a user that has received the one of the stimulation programs or sets of stimulation parameters. In at least some embodiments, the system is configured and arranged, via the at least one processor and communications arrangement, to receive a review or recommendation for at least one of the stimulation programs or sets of stimulation parameters and to store, on the at least one memory, the score or rating in conjunction with that at least one of the stimulator programs or sets of stimulation parameters.

In at least some embodiments, the at least one processor is configured and arranged to analyze the stimulation programs or sets of stimulation parameters and, via at least one machine learning algorithm, generate a new stimulation program or set of stimulation parameters to improve treatment efficacy. In at least some embodiments, the at least one processor is configured and arranged to analyze the stimulation programs or sets of stimulation parameters and, via at least one machine learning algorithm, generate a modified stimulation program or set of stimulation parameters to improve treatment efficacy. In at least some embodiments, the at least one processor is configured and arranged to analyze the stimulation programs or sets of stimulation parameters and, via at least one machine learning algorithm, generate a new stimulation program or set of stimulation parameters based on at least one of a patient characteristic; disease or disorder or condition; symptom or symptoms; stimulation device or lead type; or electrode or lead location.

In at least some embodiments, the system is configured and arranged to permit a user to purchase at least one of the stimulation programs or sets of stimulation parameters and to provide, via the at least one processor and communications arrangement, the purchased at least one of the stimulation programs or sets of stimulation parameters to the user. In at least some embodiments, the system is configured and arranged to categorize the stimulation programs or sets of stimulation parameters and to permit the user to access the stimulation programs or sets of stimulation parameters via the categorization. In at least some embodiments, the categorization is based on at least one of type of disease or disorder or condition; type of stimulation; area of symptom manifestation; lead or electrode placement; or physical activity type.

Another embodiments is a computer-based method, where actions are performed by a processor, the actions including: receiving a plurality of stimulation programs or a plurality of sets of stimulation parameters from a plurality of different devices remote from the processor and used to stimulate a plurality of different patients; storing the plurality of stimulation programs or plurality of sets of stimulation parameters on at least one memory; and retrieve the stored stimulation programs or sets of stimulation parameters from the at least one memory when requested by user.

In at least some embodiments, the actions further include receiving a score or rating for at least one of the stimulation programs or sets of stimulation parameters and storing, on the at least one memory, the score or rating in conjunction with that at least one of the stimulator programs or sets of stimulation parameters. In at least some embodiments, the actions further include requesting the score or rating for at least one of the stimulation programs or sets of stimulation parameters from a user that has received the one of the stimulation programs or sets of stimulation parameters. In at least some embodiments, the actions further include receiving a review or recommendation for at least one of the stimulation programs or sets of stimulation parameters and storing, on the at least one memory, the score or rating in conjunction with that at least one of the stimulator programs or sets of stimulation parameters.

In at least some embodiments, the actions further include analyzing the stimulation programs or sets of stimulation parameters and, via at least one machine learning algorithm, generating a new stimulation program or set of stimulation parameters to improve treatment efficacy. In at least some embodiments, the actions further include analyzing the stimulation programs or sets of stimulation parameters and, via at least one machine learning algorithm, generating a modified stimulation program or set of stimulation parameters to improve treatment efficacy. In at least some embodiments, the actions further include analyzing the stimulation programs or sets of stimulation parameters and, via at least one machine learning algorithm, generating a new stimulation program or set of stimulation parameters based on at least one of a patient characteristic; disease or disorder or condition; symptom or symptoms; stimulation device or lead type; or electrode or lead location.

In at least some embodiments, the actions further include permitting a user to purchase at least one of the stimulation programs or sets of stimulation parameters and providing the purchased at least one of the stimulation programs or sets of stimulation parameters to the user. In at least some embodiments, the actions further include categorizing the stimulation programs or sets of stimulation parameters and to permit the user to access the stimulation programs or sets of stimulation parameters via the categorization.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 7 is a flowchart of one embodiment of a method for adjusting stimulation parameters, according to the invention;

FIG. 8 is a flowchart of one embodiment of a method for testing a range of stimulation parameters, according to the invention;

FIG. 9 is a flowchart of one embodiment of a method for requesting patient authorization for using patient data, according to the invention;

FIG. 10 is a flowchart of another embodiment of a method for obtaining stimulation recommendations, according to the invention;

DETAILED DESCRIPTION

The present invention is directed to the area of implantable electrical stimulation systems and methods of making and using the systems. The present invention is also directed to implantable electrical stimulation systems include devices or methods for providing feedback regarding electrical stimulation, as well as methods of making and using the electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference in their entireties.

An electrical stimulation system can include a local or non-local network of devices that can be used in a session to program, visualize or interact during a medical office procedure, such as a session to program a neurostimulator. In at least some embodiments, the system allows a patient to provide feedback on the effects of the therapy while the clinician or programmer adjusts the parameters of the medical device.

For example, the clinician or programmer uses an external programming unit that communicates (directly or through a secondary device) with an implantable control module that delivers therapy or stimuli to a patient. The clinician or programmer perceives or receives from the patient feedback regarding the clinical effects of the stimuli. The feedback can then be recorded into the external programming unit or other components of the system (locally or remotely). This feedback is utilized to define a clinical effects map that correlates therapy delivered with the clinical effects experienced. Alternatively or additionally, both the programmer and the patient may input the clinical effects into the system. The patient may provide feedback to the programming unit via a patient interface unit. Patient feedback may also be recorded as bio-signals from the patient (EEG, EMG, CMAP, ECG, skin resistance, muscle tone, movement, vibration, rigidity, temperature, breathing, oxygen levels, chemical concentrations, skin resistance, gait, skin tone, force, pressure, and the like.)

Figure 1:
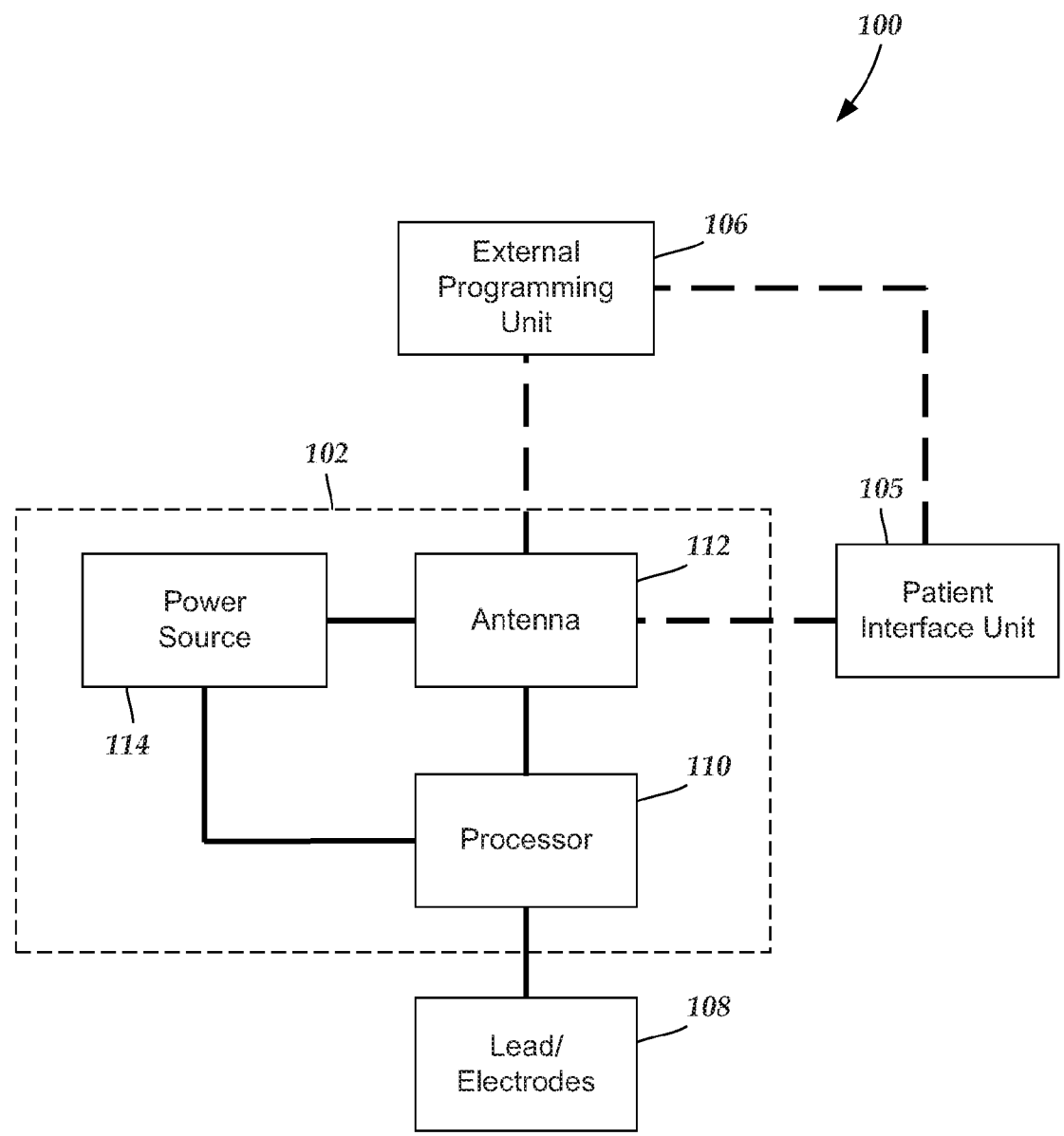
FIG. 1 is a schematic block diagram of one embodiment of an electrical stimulation system, according to the invention.

FIG. 1 illustrates schematically one embodiment of an electrical stimulation system 100 that includes an implantable control module (e.g., an implantable electrical stimulator or implantable pulse generator) 102, one or more leads 108 with electrodes, one or more external programming units 106, and a patient interface unit 105. Alternatively, the implantable control module 102 can be part of a microstimulator with the electrodes disposed on the housing of the microstimulator. The microstimulator may not include a lead or, in other embodiments, a lead may extend from the microstimulator. It will be understood that the electrical stimulation system can include more, fewer, or different components and can have a variety of different configurations including those configurations disclosed in the references cited herein. For example, although FIG. 1 illustrates one external programming units 106, one control module 102, and one patient interface unit 105, it will be understood that the system can include more than one external programming unit, more than one control module, and more than one patient interface unit.

The lead 108 is coupled, or coupleable, to the implantable control module 102. The implantable control module 102 includes a processor 110, an antenna 112 (or other communications arrangement), a power source 114, and a memory 116, as illustrated in FIG. 1.

Figure 2:
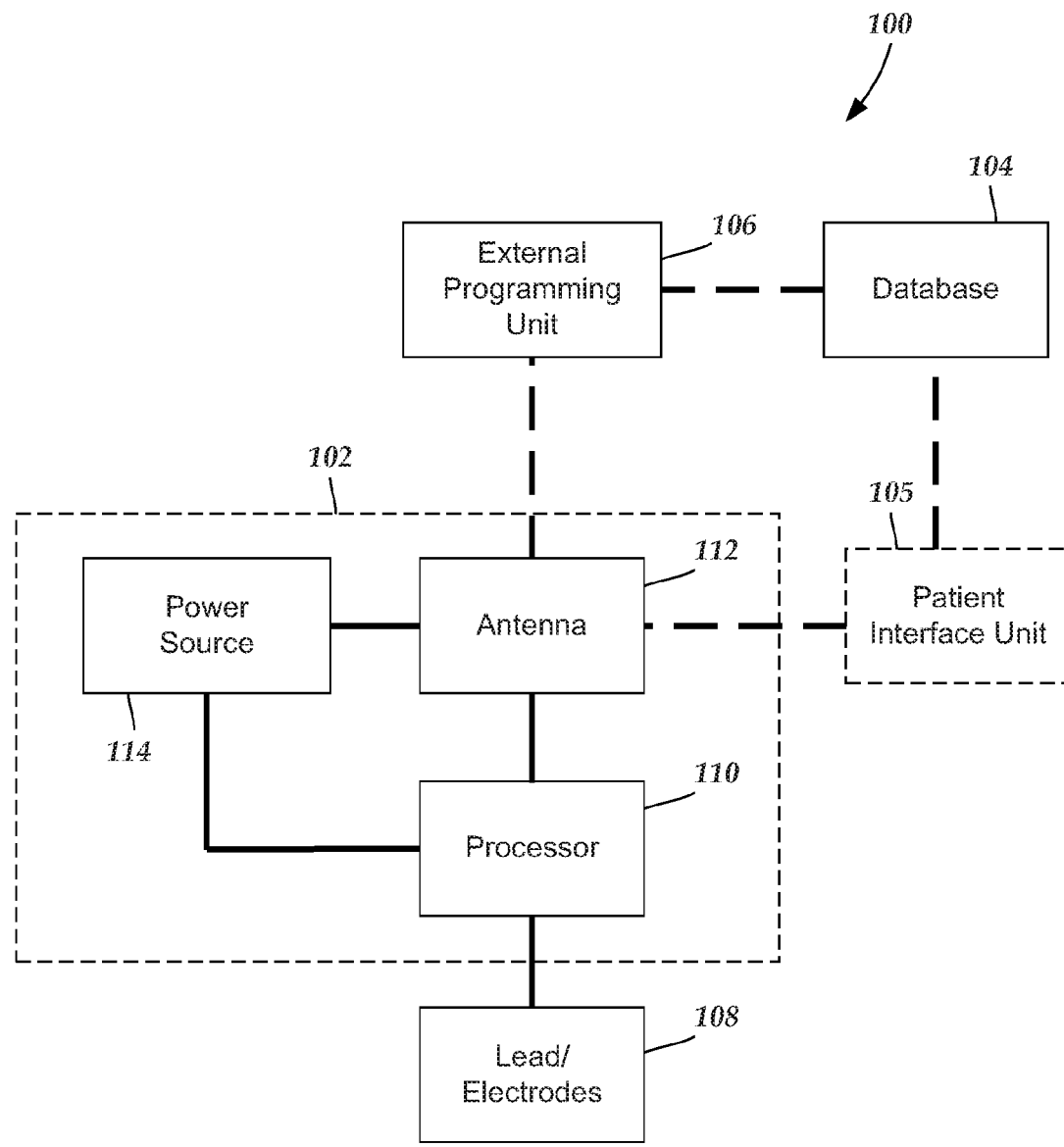
FIG. 2 is a schematic block diagram of another embodiment of an electrical stimulation system, according to the invention.
Figure 3A:
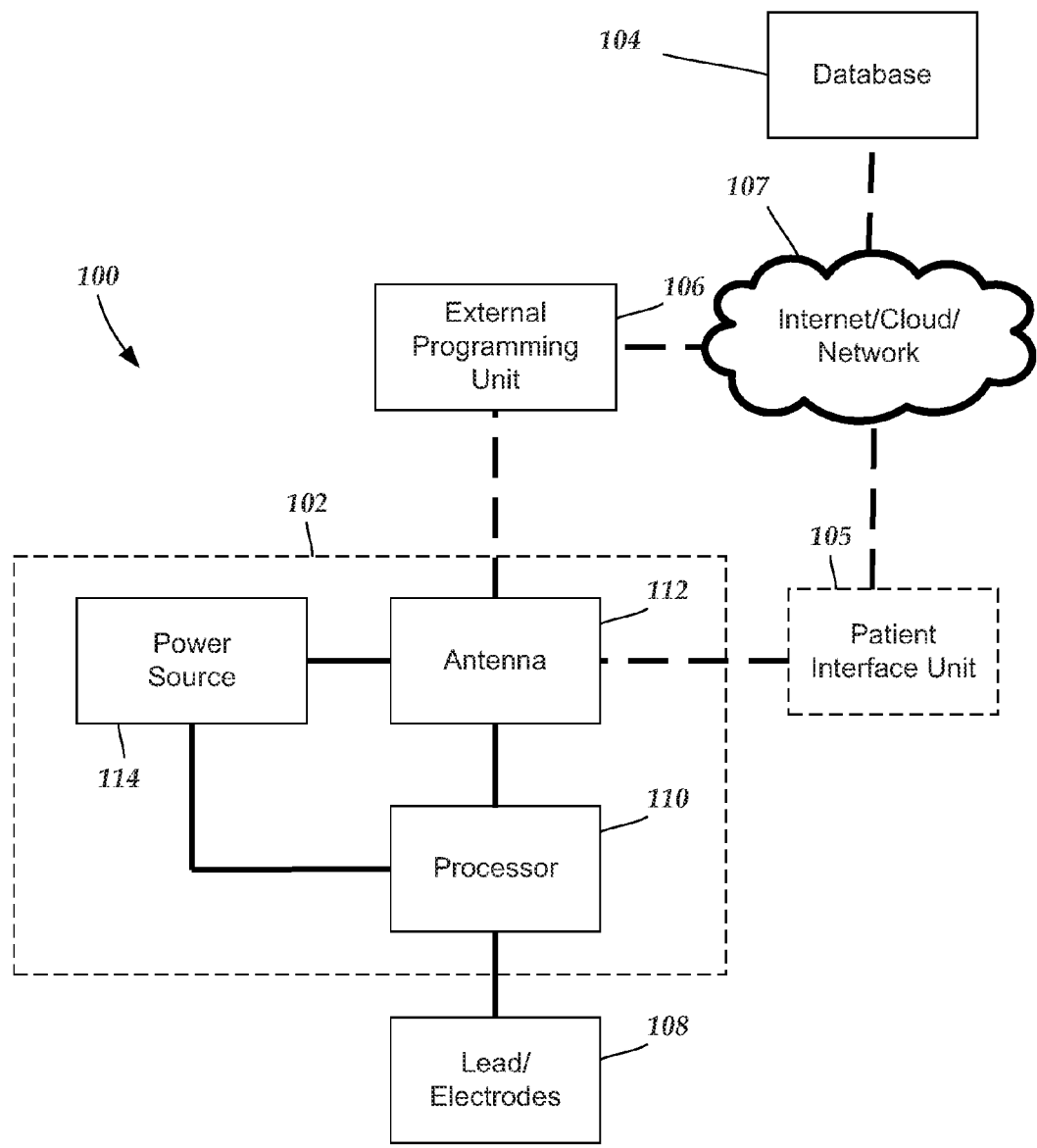
FIG. 3A is a schematic block diagram of another embodiment of an electrical stimulation system, according to the invention.
Figure 6:
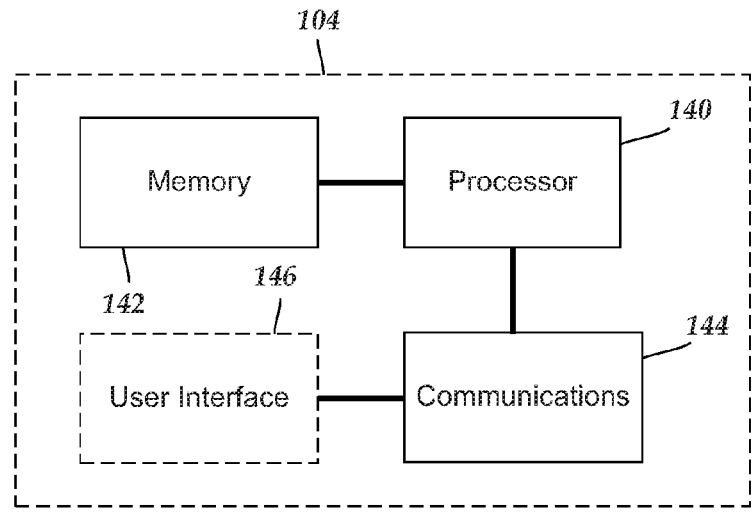
FIG. 6 is a schematic block diagram of one embodiment of a database, according to the invention.

FIG. 2 illustrates another embodiment that includes a database 104 with communicates with the external programming unit 106 and optional patient interface unit 105. FIG. 3A illustrates another embodiment in which the external programming unit 106 and optional patient interface unit 105 communicate through the Internet, a cloud, or a local or wide area network 107 (including wireless local or wide area networks) or any combination thereof, or any other suitable intermediary or combination of intermediaries, to the database 104.

Figure 4:
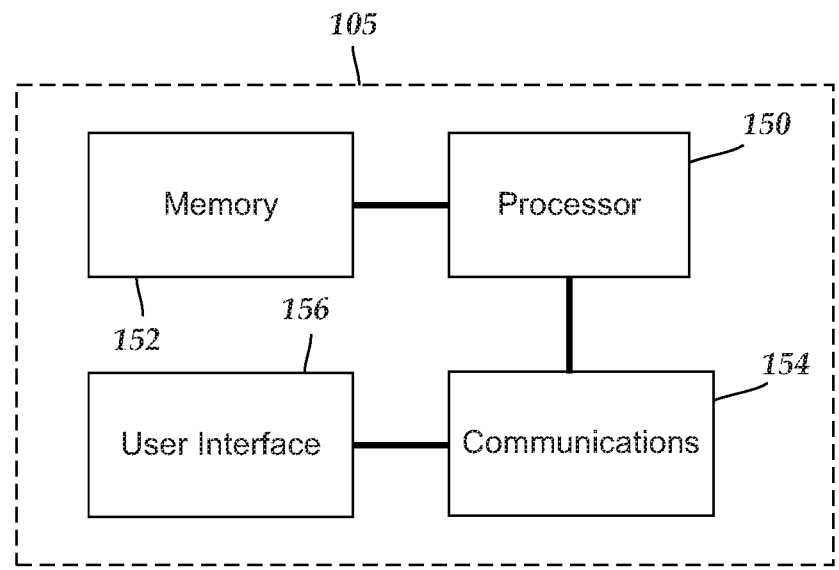
FIG. 4 is a schematic block diagram of one embodiment of a patient interface unit, according to the invention.

One example of a patient interface unit 105 is illustrated in FIG. 4 and includes a processor 150, a memory 152, a communications arrangement 154 (such as an antenna or any other suitable communications device such as those described below), and an optional user interface 156. Suitable devices for use as a patient interface unit can include, but are not limited to, a computer, a tablet, a mobile telephone, a personal desk assistant, a dedicated device for external programming, remote control, or the like. In at least some embodiments, the patient interface unit 105 can also be an external programming unit.

Figure 5:
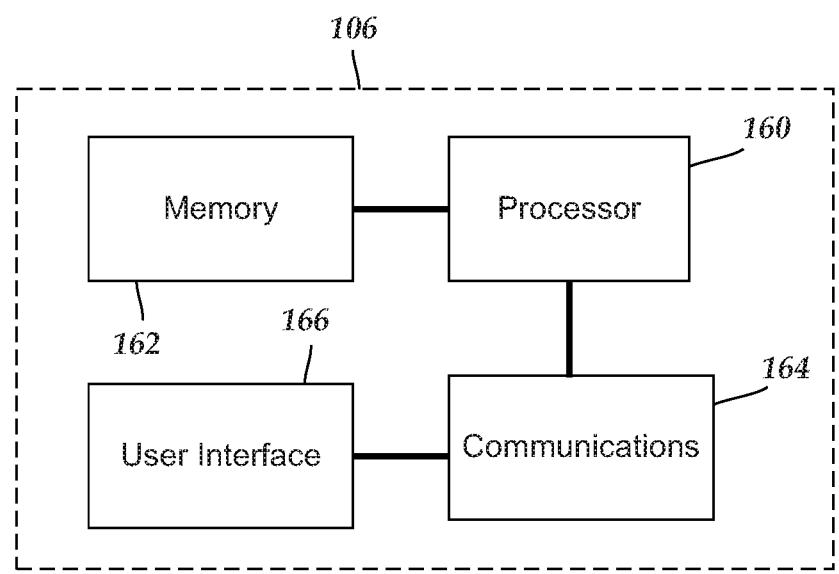
FIG. 5 is a schematic block diagram of one embodiment of an external programming unit, according to the invention.

One example of an external programming unit 106 is illustrated in FIG. 5 and includes a processor 160, a memory 162, a communications arrangement 164 (such as an antenna or any other suitable communications device such as those described below), and a user interface 166. Suitable devices for use as an external programming unit can include, but are not limited to, a computer, a tablet, a mobile telephone, a personal desk assistant, a dedicated device for external programming, remote control, or the like. It will be understood that the external programming unit 106 and patient interface unit 105 can include a power supply or receive power from an external source or any combination thereof. In at least some embodiments, the external programming unit 106 may also be a patient interface unit.

One example of a database 104 is illustrated in FIG. 4 and includes a processor 140, a memory 142, a communications arrangement 144 (such as an antenna or any other suitable communications device such as those described below), and an optional user interface 146. Suitable devices for use as a remote data storage unit can include, but are not limited to, a computer, a tablet, a server or server farm, a dedicated device for data storage, a hard drive, cloud storage arrangement, or the like. It will be understood that the external programming unit 106 and remote data storage unit 104 can include a power supply or receive power from an external source or any combination thereof. In some embodiments, the database 104 can also act as a remote storage unit for storage and retrieval of stimulation parameters and other stimulation data. Examples of remote storage units and their use and operation in electrical stimulation systems can be found in U.S. Provisional Patent Application Ser. No. 62/028,688, incorporated herein by reference in its entirety.

Methods of communication between devices or components of a system can include wired or wireless (e.g., RF, optical, infrared, near field communication (NFC), Bluetooth™, or the like) communications methods or any combination thereof. By way of further example, communication methods can be performed using any type of communication media or any combination of communication media including, but not limited to, wired media such as twisted pair, coaxial cable, fiber optics, wave guides, and other wired media and wireless media such as acoustic, RF, optical, infrared, NFC, Bluetooth™ and other wireless media. These communication media can be used for communications units 144, 154, 164 or as antenna 112 or as an alternative or supplement to antenna 112.

Turning to the control module 102, some of the components (for example, a power source 114, an antenna 112, and a processor 110) of the electrical stimulation system can be positioned on one or more circuit boards or similar carriers within a sealed housing of the control module (implantable pulse generator) if desired. Any power source 114 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like including the power sources described in U.S. Pat. No. 7,437,193, incorporated herein by reference in its entirety.

As another alternative, power can be supplied by an external power source through inductive coupling via the antenna 112 or a secondary antenna. The external power source can be in a device that is mounted on the skin of the user or in a unit that is provided near the user on a permanent or periodic basis.

If the power source 114 is a rechargeable battery, the battery may be recharged using the antenna 112, if desired. Power can be provided to the battery for recharging by inductively coupling the battery through the antenna to a recharging unit external to the user.

A stimulation signal, such as electrical current in the form of electrical pulses, is emitted by the electrodes of the lead 108 (or a microstimulator) to stimulate neurons, nerve fibers, muscle fibers, or other body tissues near the electrical stimulation system. Examples of leads are described in more detail below. The processor 110 is generally included to control the timing and electrical characteristics of the electrical stimulation system. For example, the processor 110 can, if desired, control one or more of the timing, frequency, strength, duration, and waveform of the pulses. In addition, the processor 110 can select which electrodes can be used to provide stimulation, if desired. In some embodiments, the processor 110 selects which electrode(s) are cathodes and which electrode(s) are anodes. In some embodiments, the processor 110 is used to identify which electrodes provide the most useful stimulation of the desired tissue.

With respect to the control module 102, patient interface unit 105, external programming unit 106, and database unit 104, any suitable processor 110, 140, 150, 160 can be used in these devices. For the control module 102, the processor 110 is capable of receiving and interpreting instructions from an external programming unit 106 that, for example, allows modification of pulse characteristics. In the illustrated embodiment, the processor 110 is coupled to the antenna 112. This allows the processor 110 to receive instructions from the external programming unit 106 to, for example, direct the pulse characteristics and the selection of electrodes, if desired. The antenna 112, or any other antenna described herein, can have any suitable configuration including, but not limited to, a coil, looped, or loopless configuration, or the like.

In one embodiment, the antenna 112 is capable of receiving signals (e.g., RF signals) from the external programming unit 106. The external programming unit 106 can be a home station or unit at a clinician's office or any other suitable device. In some embodiments, the external programming unit 106 can be a device that is worn on the skin of the user or can be carried by the user and can have a form similar to a pager, cellular phone, or remote control, if desired. The external programming unit 106 can be any unit that can provide information to the control module 102. One example of a suitable external programming unit 106 is a computer operated by the user or clinician to send signals to the control module 102. Another example is a mobile device or an application on a mobile device that can send signals to the control module 102

The signals sent to the processor 110 via the antenna 112 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the control module 102 to cease operation, to start operation, to start charging the battery, or to stop charging the battery.

Optionally, the control module 102 may include a transmitter (not shown) coupled to the processor 110 and the antenna 112 for transmitting signals back to the external programming unit 106 or another unit capable of receiving the signals. For example, the control module 102 may transmit signals indicating whether the control module 102 is operating properly or not or indicating when the battery needs to be charged or the level of charge remaining in the battery. The processor 110 may also be capable of transmitting information about the pulse characteristics so that a user or clinician can determine or verify the characteristics.

Any suitable memory 116, 142, 152, 162 can be used for the respective components of the system 100. The memory 116, 142, 152, 162 illustrates a type of computer-readable media, namely computer-readable storage media. Computer-readable storage media may include, but is not limited to, nonvolatile, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The user interfaces 156, 166 of the external programming unit 106 and patient interface unit 105 and optional user interface 146 of the database 104 can be, for example, a keyboard, mouse, touch screen, track ball, joystick, voice recognition system, or any combination thereof, and the like. Alternatively or additionally, the user interfaces 156, 166 of the external programming unit 106 and of the patient interface unit 105 can include one or more microphones, sensors, cameras, or the like to obtain patient feedback. For example, the patient may provide feedback verbally (e.g. voice command recognition, voice recordings) or visually (e.g. video of patient, non-touch gesture recognition, or the like). In at least some embodiments, at least a portion (or even all of) the patient feedback may be recorded as bio-signals from the patient (EEG, EMG, CMAP, ECG, skin resistance, muscle tone, movement, vibration, rigidity, temperature, breathing, oxygen levels, chemical concentrations, skin resistance, gait, skin tone, force, pressure, or the like.) In at least some embodiments, such as those illustrated in FIGS. 2 and 3 without the optional patient interface unit, patient feedback can be provided by the clinician or other user through the external programming unit 106.

In at least some embodiments, the patient interface unit 105 may also have controls to adjust parameters of the stimulation, which are optionally limited to an acceptable range by the clinician (using the patient interface unit or external programming unit) or by default settings of the electrical stimulation system or control module or any other suitable mechanism. Such parameters can include, for example, one or more of stimulation amplitude range, stimulation frequency range, stimulation pulse width, stimulation duration, interval between delivery of stimulation, electrode combinations, selection of anode(s) and cathode(s), or the like or any combination thereof.

In at least some embodiments, as the person delivering therapy adjusts stimulation parameters using the external programming unit 106, the patient can then use the patient interface unit 105 to identify the effects of the stimulation parameters. For example, the patient can indicate in which areas of the body there is perception of stimulation (e.g. paresthesia) or indicate a pain level or indicate a score for satisfaction with treatment, or any combination thereof. In at least some embodiments, the patient interface unit 105 may also allow the patient to input areas where the patient needs or desires more stimulation and areas where the patient needs or desires less stimulation (for example, areas with side effects). This information can be provided to the external programming unit 106 for the programmer to adjust stimulation parameters.

In at least some embodiments, the system utilizes a figure of merit of the adequacy, or a rating, of the stimulation provided. The figure of merit can be based on, for example, one or more of the following: therapeutic effect, patient satisfaction, level or presence of side effects, patient dissatisfaction, or the like or any combination thereof. The figure of merit can be, for example, a numerical value, an alpha-numerical rating, a descriptive rating, or any other suitable rating mechanism or any combination thereof. The figure of merit may be provided by the clinician, the patient, or both and can be input through the external programming unit 106, patient interface unit 105, or other device or any combination of these or other devices. In at least some embodiments, the figure of merit can be used to enhance, adjust, or guide stimulation delivery.

The figure of merit may be determined from multiple ratings provided by the clinician, the patient, or both. In at least some embodiments, the determination of a figure of merit may employ different weights to different parameters in the calculation. For example, the determination may add more value to certain preferred clinical outcomes, may add more negative value to particular side effects, may add less negative value to power consumption, or the like. The weights and parameters entering the figure of merit may be defined by the users of the system (e.g. patient, clinician, programmer, or any combination thereof) or may be pre-set by the system. The system may allow different users to define different figures of merit that can be optionally shared via the system.

FIG. 7 is a flowchart of one embodiment of a method of adjusting stimulation parameters. In step 702, patient feedback is requested. The request can be made on the external programming unit, patient interface unit, or using any other suitable device or method, or any combination thereof. In step 704, the patient feedback is obtained. The patient may provide the feedback directly to the system through, for example, the patient interface unit or may provide the feedback to the clinician who inputs the feedback through, for example, the external programming unit. In step 706, the system analyzes the feedback and provides recommendations for adjusting the stimulation parameters based on the patient feedback. In some embodiments, the analysis, or portions of the analysis, may be performed by the external programming unit or another local device. In some embodiments, the analysis, or portions of the analysis, can be performed using a remote device.

In at least some embodiments, the system may allow creation of different therapeutic options based, for example, on different figures of merit or situations for the patient. Each therapeutic option may have one or more different stimulation parameters from other therapeutic options. For example, the system may provide or allow different stimulation programs for one or more of the following conditions or situations: sleep, walking, condition exacerbation, acute episodes, preventative therapies, activity based, and the like. In at least some embodiments, the patient user interface 105 or the external programming unit 106 may be designed to create multiple areas of stimulation and multiple programs to target different areas.

In at least some embodiments, the stimulation controls of the external programming unit 106 or, optionally, the patient interface unit 105 may be designed to allow changing the shape of the stimulation area, size of the stimulation area, strength of the stimulation, perception pattern (for example, type of sensation or no sensation) of the stimulation, or the like, or any combination thereof. In at least some embodiments, the external programming unit 106 or, optionally, the patient interface unit 105 may allow a user to move the stimulation to different anatomical areas (for example, using directional controls, such as arrows, or a joystick or mouse or other mechanism) or by marking areas in a map representing the body. In at least some embodiments, the external programming unit 106 or, optionally, the patient interface unit 105 may allow a use to increment or decrement stimulation in certain areas of the body or to add or remove stimulation from certain areas of the body. In at least some embodiments, the external programming unit 106 or, optionally, the patient interface unit 105 may allow a user (for example, a clinician or a patient) to increase or decrease the intensity of stimulation in areas of the body. In at least some embodiments, these areas can be mapped by the patient using the patient interface unit 105.

In at least some embodiments, a human figure, or parts of human anatomy, can be depicted in 2-dimensional and/or 3-dimensional representations on the patient user interface unit 105 or the external programming unit 106 to allow the user (for example, a patient or a clinician) to input areas of the body that, for example, experience stimulation-induced effects (for example, where stimulation is perceived or where stimulation is evidenced), experience pain, are desired stimulation areas, are areas where stimulation is not desired, are areas where side effects occur, or the like or any combination thereof. In at least some embodiments, the areas of the body can be marked based on level of intensity of stimulation, pain, or side effects or any other suitable parameter. In at least some embodiments, the user can indicate different levels of intensity, for example, areas of intense pain or mild pain, or areas of intense stimulation or mild stimulation). It will be recognized that more than two different levels of intensity can be represented. In addition, in at least some embodiments, aspects of the reported pain, stimulation, or side effects (or any combination thereof) may be recorded in addition to the intensities of said effects. For example, pain quality (for example, tingling, burning, stabbing, shooting, throbbing, or the like), stimulation quality (for example, tingling, buzzing, hot, cold, cool, warm, or the like), other characteristics (for example, worst pain, overall pain, pain that is 'superficial' or 'deep', stimulation effects which are 'superficial' or 'deep', or the like), or any combination thereof can be recorded.

FIG. 8 is a flowchart of one embodiment of a method of testing a range of stimulation parameters. In step 802, the patient is stimulated over a range of stimulation parameters. In some embodiments, only a single stimulation parameter (for example, stimulation amplitude, stimulation duration, selection of electrodes) is varied over a range. In other embodiments, more than one stimulation parameter is varied. In step 804, the patient feedback is obtained. The patient may provide the feedback directly to the system through, for example, the patient interface unit or may provide the feedback to the clinician who inputs the feedback through, for example, the external programming unit. In step 806, the system analyzes the feedback and presents the clinical effects (for example, patient feedback, stimulation efficacy, presence of side effects, strength of side effects, or any combination thereof) for the range of stimulation parameters. In some embodiments, the system may also provide recommendations for the stimulation parameters based on the patient feedback. In some embodiments, the analysis, or portions of the analysis, may be performed by the external programming unit or another local device. In some embodiments, the analysis, or portions of the analysis, can be performed using a remote device.

In at least some embodiments, the system stores the different therapeutic options, clinical effects map, figures of merit of the particular patient in one or more of the control module 102, the external programming unit 106, patient user interface 105, or remote database 104. In at least some embodiments, the clinical effects observed by the clinician or reported by the patient are stored in relation to the particular set of parameters associated therewith. The parameters of the stimulation can include the stimulation parameters at the time of feedback or may also include historical information, such as the parameters used for stimulation delivered over a period of time.

In at least some embodiments, the external programming unit 106, control module 102, or patient interface unit 105 (or any combination thereof) may be configured to adjust the stimulation parameters in a selected pattern either automatically or semi-automatically (with some user control over selection of which parameters to test or sets of initial parameters) to create a map of clinical effects over a related set of stimulation conditions. For example, an algorithm may guide several sets of parameters and stimulation combinations in a given order and record clinical effects as the different parameter sets are exercised. As another example, an algorithm can adjust one or more of amplitude, frequency, duration, electrode selection, or the like or any combination thereof to obtain a map of clinical effects for varied stimulation parameters. In at least some embodiments, the patient, user, or system can provide information, ratings, or figures of merit for the different sets of stimulation parameters.

The system can also incorporate demographics (for example, age, gender, ethnicity, height, weight, or the like) and disease-specific details (for example, pain etiology(ies), number of prior back surgeries, relevant diagnoses, imaging findings, or the like) in the information provided to the external programming unit 106, control module 102, or patient interface unit 105 (or any combination thereof).

In at least some embodiments, the system may also be capable of receiving medical imaging information (for example, photographs, video, MRI images, CT scans, ultrasound images, anatomical atlases, or the like) and device information. The system may be configured to allow a user to upload MRI scans, CT scans, ultrasound images, or other visualization information of the anatomical targets for stimulation. In at least some embodiments, the system or a user may also correlate this visualization information to the position of the lead and electrical contacts to aid in the recommendation of stimulation targets and electrode combinations.

In at least some embodiments, information obtained from a programming or patient interactive session can be recorded and stored on one or more of the control module 102, the external programming unit 106, patient user interface 105, or remote database 104. This information may be used to provide additional statistical data to correlate stimulation parameters, targets of stimulation, anatomical placements, lead configurations, diagnostics, symptoms, patient characteristics, or the like. This information may also be used to inform a statistical-based algorithm that aggregates the information and calculates potential or recommend lead or electrode configurations for the patient. Such configurations, the underlying information, or portions of the information may be made available to other programmers, clinicians, or patients.

In at least some embodiments, the system may use information (for example, stimulation parameters, patient or clinician feedback, figures of merit, ratings, or the like) inputted to one or more of the control module 102, the external programming unit 106, patient user interface 105, or remote database 104 to calculate derived metrics that can be used by the programmer to assess programming effectiveness. Examples include stimulation effectiveness, pain/paresthesia concordance, worst pain/paresthesia concordance, quantification of the degree to which the pain that has 'neuropathic' descriptors assigned to it by the patient is covered with stimulation, quantification of the degree to which pain that has 'nociceptive' or 'pain' descriptors assigned to it by the patient is covered with stimulation, side effect correlation to parameters or location, or the like.

In at least some embodiments, the system can use the patient- or clinician-provided feedback to automatically adjust stimulation parameters. For example, if the patient or clinician marks an area as too intense the system may automatically reduce the stimulation amplitude in that area (by changing electrode combinations or electrical parameters of the electrodes), or it could recommend a next settings of parameters which the user can accept or migrate to. In at least some embodiments, the system can determine or present a "target volume of activation" and the user may adjust stimulation parameters to overlap the target.

In at least some embodiments, the system contains information regarding targets based on historical and statistical data within a single patient or across many patients. For example, a depiction of a human and selection of areas of pain can produce a pain map that can be utilized to input areas of pain (or other symptoms) by the patient or clinician or both. In at least some embodiments, the system can use this pain map to provide recommended target volumes of activation (where electric current should be delivered) or recommended initial stimulation parameters or recommended stimulation parameter ranges for testing. This information can be used to plan for the surgical procedure to implant the control module and lead(s) and programming of the control module.

In at least some embodiments, the feedback provided or perceived from the patient or clinician is mapped in the patient interface unit 105, external programming unit 106, or database 104 or any combination thereof and can be available to be used by the system to provide feedback to the user to aid in the stimulation adjustment. In at least some embodiments, the system may use the information to provide a recommended next step for adjustment of stimulation parameters or other adjustment to therapeutic treatment. In at least some embodiments, the system may use the information and aggregate it with information from the same or other patients to create a statistical estimation of clinical effects in relation to stimulation parameters, user characteristics, or any combination thereof.

In at least some embodiments, the system transmits data collected from the patient (for example, clinical effects, patient or clinician feedback, stimulation parameters, or any combination thereof) to be transmitted to the database 104. The information in the database 104 may be used for aggregation and recommendation of stimulation adjustments at a different clinical session or may be provided to the patient or clinician to download into his/her devices (e.g., control module 102, the external programming unit 106, patient user interface 105, personal devices or database, or the like or any combination thereof).

For data aggregation, the user (for example, clinician, patient, or other user) may choose to aggregate a group of data (for example, data from a particular patient set to a given medical center or centers) or may choose to aggregate data from a larger group of patients. Data aggregation can be executed from a local system (relative to the clinician, patient, site of surgery, or the like) or may be done remotely (e.g. remote database and cloud computing).

In at least some embodiments, the system has a feature for the patient to authorize the information to be used in the aggregation of data or exported for further analysis. For example, the patient may produce an electronic signature, paper signature that is recorded, video or audio authorizing the aggregation, or the like. If the patient authorizes data aggregation, the patient's data can be used for analysis by the system to inform programming or stimulation delivery to other patients or to analyze further. If the patient does not authorize the information to be used, the system will exclude the patient's data from the aggregation of data from other patients. In at least some embodiments, the system excludes patient identification data for aggregation, export or analysis.

FIG. 9 is a flowchart of one embodiment of a method of obtaining patient authorization. In step 902, the system requests patient authorization. The request can be made through the clinician, through the external programming unit, or the patient interface unit or any other suitable mechanism. In step 904, the patient authorization is obtained. In at least some embodiments, that authorization is in the form of an electronic signature, paper signature that is recorded, video or audio authorizing the aggregation, or the like. In step 906, the patient authorization and authorized patient data is submitted to the database. This submission of authorization and data may be performed simultaneously or performed at different times. If the data has been previously submitted to the database, the patient's authorization may be used to allow the previously submitted data to be aggregated with other data.

In at least some embodiments, the system may also allow experienced programmers of the stimulation system to propose stimulation parameter or lead configurations which can be downloaded by other users of the system.

In at least some embodiments, multiple external programming units 106, patient interface units 105, or any combination thereof can be connected either locally or remotely into a network (local or wide area or virtual) allowing multiple programmers or users at the same time. In at least some embodiments, when multiple programmers are using a system, the system can be configured to allow several programmers to work at the same time or at different times. In at least some embodiments, the system can also be configured to allow different priorities between users. In at least some embodiments, the system can also be configured to allow particular functions to take precedence regardless of who is the user (for example, an emergency stimulation shut down command).

In at least some embodiments, the aggregation of data can include the creation of target stimulation maps for particular pain conditions. The system can aggregate effective stimulation parameters for many patients who experience pain due to different conditions and different locations in the body. The system (automatically, semi-automatically, or with clinician input) can evaluate, based on figures of merit or other feedback or data from each of the patients, and provide a statistical target area to stimulate in the spinal cord of a patient to ensure maximum likelihood of success, based on the figure of merit. In at least some embodiments, a clinician can then input the pain condition of the patient and read from the target stimulation map the recommended stimulation locations or parameters or both and a statistical distribution of results. In at least some embodiments, the system can provide a visual anatomical representation of the target area (for example, as a single point, a surface, an anatomical structure, or a volume). The target of activation may also be determined via functional outcomes of stimulation (e.g. one vertebral space above area where toe flexion occurs during stimulation). In at least some embodiments, this information can be used to plan the placement of the electrodes. In at least some embodiments, once the electrodes are in place, the location of the electrodes relative to the spinal cord can be input to the system. In at least some embodiments, the system can then recommend one or more sets of stimulation parameters or parameter ranges to place stimulation in the target area.

In at least some embodiments, the target area may be represented in the system and a volume of activation based on current stimulation parameters to visually indicate the amount of overlap (and non-overlap) of target volume and volume of activation. In at least some embodiments, the system may provide surface or volumetric measures of overlap and non-overlap. The user can use the stimulation controls to place stimulation in the target or as close as adequate. This is particularly useful for indications in which patients may not feel the stimulation or in which the effects of stimulation take too long to be measured during a programming session. In at least some embodiments, the user can also use patient feedback to set the target of stimulation.

FIG. 10 is a flowchart of one embodiment of a method of obtaining recommendations for stimulation sites, parameters, or any combination therefrom from the system. In step 1002, the pain condition is input into the system using, for example, the external programming unit, the patient interface unit, or any other input device. The pain condition can be expressed in any suitable manner that is accepted by the system, such as, for example, descriptive text, selection from a list of pain sites or symptoms or other indicators, identification of pain regions on an anatomical representation, or any other suitable method of indicating the source, symptom, or site of the pain. In step 1004, the system correlates the information provided on the pain condition with the aggregated data. Such correlation may be made with the data directly or with a previously prepared correlation construct, such as a target stimulation map, pain map, pain concordance, or the like, produced using the aggregated data. In step 1006, recommendations for stimulation are provided by the system to the clinician, patient, or other user. These recommendations can include one or more of the following: stimulation site, initial stimulation parameters, stimulation parameter ranges, or any combination thereof.

It will be understood that the system can include one or more of the methods described hereinabove with respect to FIGS. 7-10 in any combination. The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks or described for the control modules, external programming units, remote data storage units, systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Figure 3B:
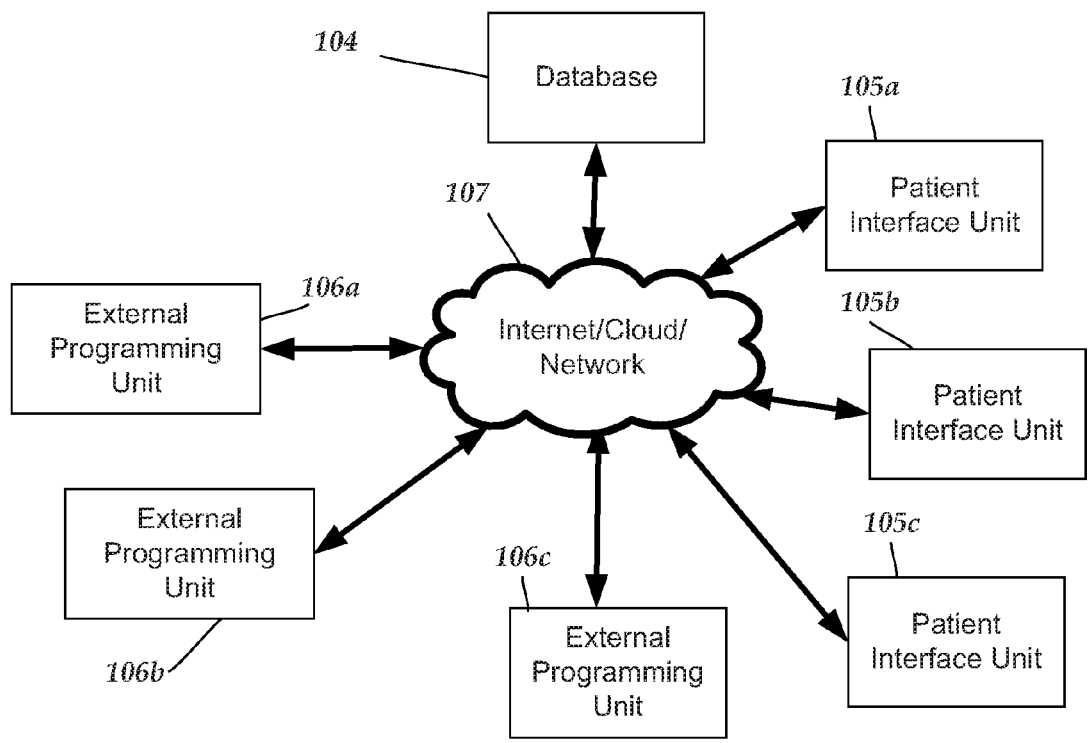
FIG. 3B is a schematic block diagram of an arrangement in which multiple devices can access a database (or store) for uploading and downloading stimulation programs, sets of stimulation parameter, or other information, according to the invention.

As indicated above, information from multiple patients can be aggregated in a database 104 and used to provide recommendations for stimulation programs, stimulation parameters, or stimulation adjustments that can be provided to one or more devices, such as, for example, a control module 102, an external programming unit 106, a patient user interface 105, personal devices or another database, or the like or any combination thereof. FIG. 3B illustrates an arrangement with multiple external programming units 106a, 106b, 106c and multiple patient user interfaces 105a, 105b, 105c that can access a database 104 through the Internet, a cloud, or a local or wide area network 107, or any combination thereof. In at least some embodiments, the database 104 can be a repository or store for obtaining stimulation programs, stimulation parameters, stimulation adjustments, therapy recommendation or guidance, lead placement information, or other information for use in providing therapy to a patient. In some embodiments, the database 104 can be a virtual therapy store or part of such a store or accessible by, or through, such a store.

The database 104 can include information such as, for example, stimulation settings, stimulation logs, program usage, implant or lead locations, and other information obtained from the control module 102, external programming unit 106, patient user interface 105, or any other suitable device. The database 104 may be directed to a specific type of stimulation therapy, such as, for example, deep brain stimulation or spinal cord stimulation or peripheral nerve stimulation, or may be directed to multiple, or all, types of stimulation therapy. The database 104 may also include information from other sources including, but not limited to, patient questionnaires; scores given by clinicians or patients for particular stimulation parameters, locations, or devices (the scores are optionally based on established scales); or any other suitable information. The database 104 may also include information gathered from internal or external sensors, such as those described in U.S. patent application Ser. No. 14/876,708 and U.S. patent application Ser. No. 15/004,771, entitled "Systems, Devices, and Methods for Electrical Stimulation Using Sensors to Adjust Stimulation Parameters," filed on even date herewith, both of which are incorporated by reference in their entireties.

In at least some embodiments, machine learning or other algorithms may be used to analyze the data on the database 104 to identify correlations between treatment efficacy and one or more stimulation variables including, but not limited to, one or more of lead or electrode placement; stimulation parameters (e.g., electrode selection, stimulation amplitude, stimulation duration, pulse frequency, pulse duration, or the like); disease or disorder or condition being treated; patient demographics (e.g., age, ethnicity, gender, activity level, weight, or the like); physical activity; or the like or any combination thereof. In at least some embodiments, these algorithms can generate new stimulation programs or sets of stimulation parameters or improve existing stimulation programs or sets of stimulation parameters. In at least some embodiments, the results of these algorithms may be tailored to a particular group of patients; one or more specific patient characteristics; one or more specific diseases or disorders or conditions; one or more specific symptoms; a lead or electrode placement; one or more specific devices or leads; one or more types of stimulation; or the like or any combination thereof.

In at least some embodiments, the database 104 may include previously uploaded stimulation programs or sets of stimulation parameters; internally or externally generated stimulation programs or sets of stimulation parameters (generated using, for example, machine learning or other algorithms); improved stimulation programs or sets of stimulation parameters; or the like or any combination thereof. In at least some embodiments, these stimulation programs or sets of stimulation parameters (or other information in the database 104) may be downloaded by a patient, clinician, or other person onto a control module 102, external programming unit 106, patient user interface 105, or any other suitable device. In at least some embodiments, downloading of some or all of the information may be limited to specific users (e.g., clinicians or paying subscribers).

In at least some embodiments, the database 104 may be part of an online virtual store (or accessed or accessible via an online virtual store) to offer patients or clinicians the stimulation programs or sets of stimulation parameters or other information for download. In at least some embodiments, the online virtual store may be similar in style or presentation to current online application stores such as iTunes™ or Google Play™ stores. In at least some embodiments, the database or store may group the stimulation programs or sets of stimulation parameters in categories based on, for example, disease or disorder or condition; type of stimulation (e.g., deep brain, spinal cord, peripheral nerve); symptom(s); area of symptom manifestation (for example, area of pain); lead or electrode placement; type of lead or device; physical activity type; or any other suitable category. In at least some embodiments, the store or database may allow patients, clinicians, or others to provide ratings for the stimulation programs or sets of stimulation parameters. In at least some embodiments, the store or database may allow patients, clinicians, or others to provide reviews or recommendations for the stimulation programs or sets of stimulation parameters. The database or store may restrict which individuals can provide reviews (e.g., clinicians or paying subscribers). In at least some embodiments, the store or database may allow patients, clinicians, or others to upload their own stimulation programs or sets of stimulation parameters with comments from the uploader. In at least some embodiments, the store or database may provide a social platform for patients, clinicians, or others, or any combination thereof to discuss the stimulation programs or sets of stimulation parameters or provide comments, suggestions, advice, or other information regarding the stimulation programs or sets of stimulation programs or how to modify the programs or parameters.

In at least some embodiments, the database store can be personalized and provide patient specific therapy recommendations. These recommendations can be made by the clinician, representative of a manufacturer or distributor of devices, or based of the patient history and analysis on neuromodulation data stored on the database or devices. In at least some embodiments, the database or store can also provide features with filtering capabilities (for example, highest or most rated programs a specific disease or disorder or condition, programs linked to a particular lead placement, alternative programs with lower energy settings, and the like) and general search functions. In at least some embodiments, the database or store can also provide a "one click" option for a patient, clinician, or other person to download any selected program to a control module 102, external programming unit 106, patient user interface 105, or any other suitable device. In some embodiments, a control module 102 or other device may include clinician-selected safety limits to limit downloaded stimulation programs or sets of stimulation parameters. In at least some embodiments, the database or store can provide free or paid options for trying new stimulation programs or sets of stimulation parameters.

In at least some embodiments, a patient can perform self-programming using a patient user interface 105. With each patient steering/navigation, the system connects to the database 104 to run algorithm and return the program parameters. In at least some embodiments, device updates or new algorithms can be deployed to the database 104 and all connected devices (e.g., control modules 102, external programming units 106, patient user interfaces 105, or other suitable devices) can download (either automatically or manually) the updates or algorithms.

Figure 11:
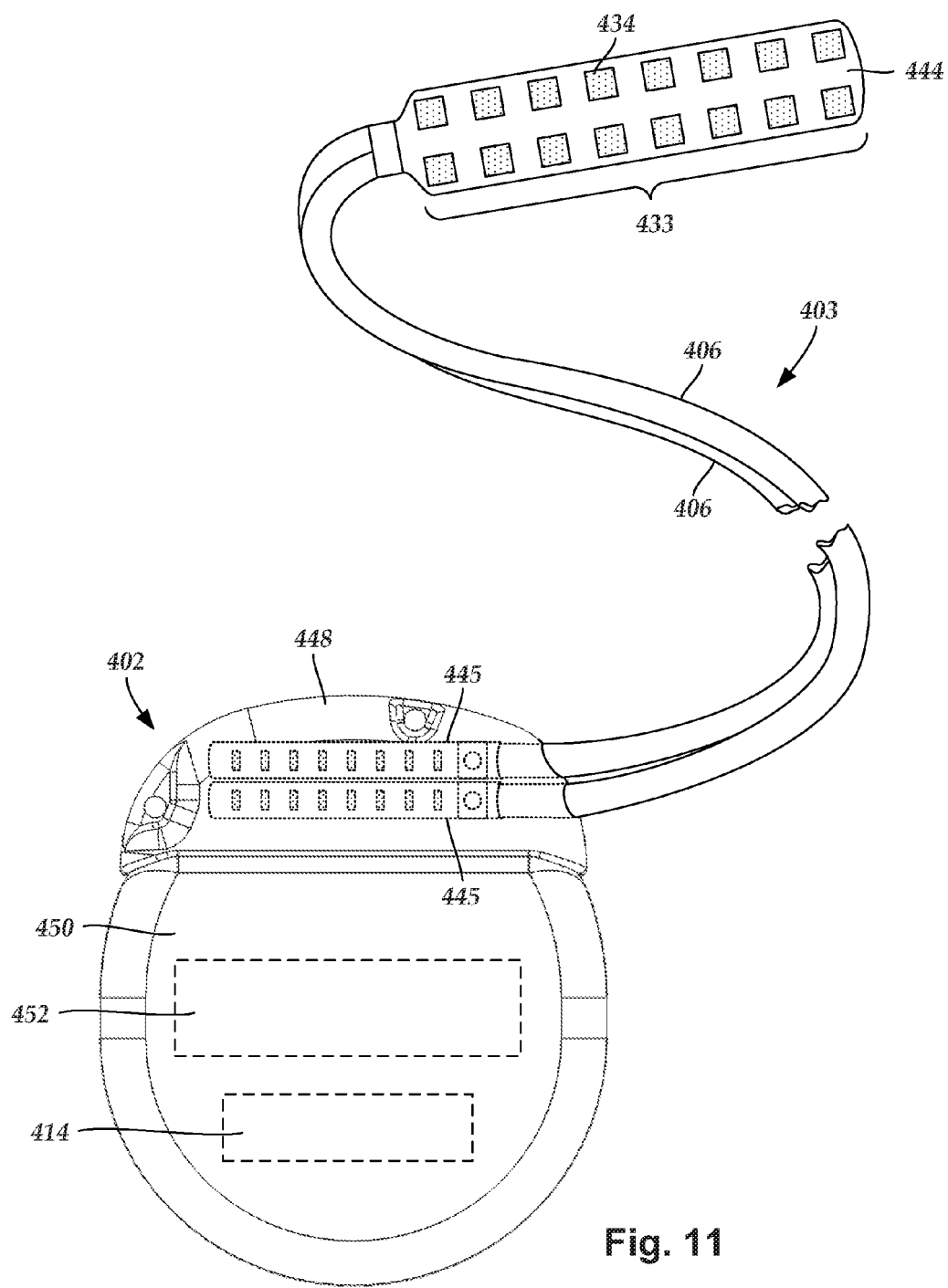
FIG. 11 is a schematic side view of one embodiment of a lead and control module, according to the invention.

FIG. 11 illustrates one embodiment of a control module 402 and lead 403. The lead 403 includes a paddle body 444 and one or more lead bodies 446. In FIG. 11, the lead 403 is shown having two lead bodies 446. It will be understood that the lead 403 can include any suitable number of lead bodies including, for example, one, two, three, four, five, six, seven, eight or more lead bodies 446. An array of electrodes 433, such as electrode 434, is disposed on the paddle body 444, and one or more terminals (e.g., 560 in FIGS. 13A and 13B) are disposed along each of the one or more lead bodies 446. In at least some embodiments, the lead has more electrodes than terminals.

Figure 12:
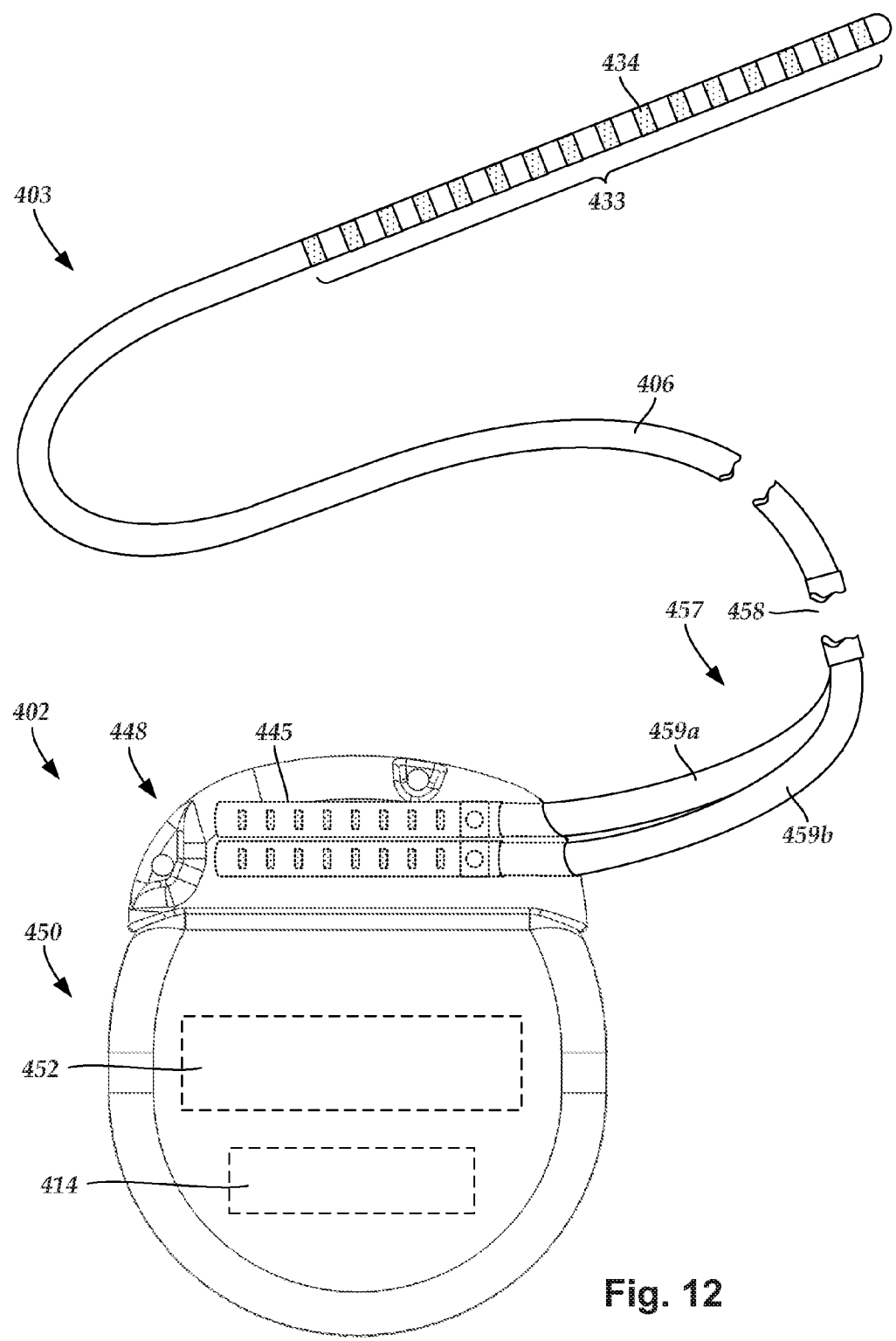
FIG. 12 is a schematic side view of another embodiment of a lead and control module, according to the invention.

FIG. 12 illustrates schematically another embodiment in which the lead 403 is a percutaneous lead. In FIG. 12, the electrodes 434 are shown disposed along the one or more lead bodies 446. In at least some embodiments, the lead 403 is isodiametric along a longitudinal length of the lead body 446.

The lead 403 can be coupled to the implantable control module 402 in any suitable manner. In FIG. 11, the lead 403 is shown coupling directly to the implantable control module 402. In at least some other embodiments, the lead 403 couples to the implantable control module 402 via one or more intermediate devices (500 in FIGS. 13A and 13B). For example, in at least some embodiments one or more lead extensions 524 (see e.g., FIG. 13B) can be disposed between the lead 403 and the implantable control module 402 to extend the distance between the lead 403 and the implantable control module 402. Other intermediate devices may be used in addition to, or in lieu of, one or more lead extensions including, for example, a splitter, an adaptor, or the like or combinations thereof. It will be understood that, in the case where the electrical stimulation system includes multiple elongated devices disposed between the lead 403 and the implantable control module 402, the intermediate devices may be configured into any suitable arrangement.

In FIG. 12, the electrical stimulation system 400 is shown having a splitter 457 configured and arranged for facilitating coupling of the lead 403 to the implantable control module 402. The splitter 457 includes a splitter connector 458 configured to couple to a proximal end of the lead 403, and one or more splitter tails 459a and 459b configured and arranged to couple to the implantable control module 402 (or another splitter, a lead extension, an adaptor, or the like).

The implantable control module 402 includes a connector housing 448 and a sealed electronics housing 450. An electronic subassembly 452 (which includes the processor 110 (see, FIGS. 1-3) and the power source 414 are disposed in the electronics housing 450. A connector 445 is disposed in the connector housing 448. The connector 445 is configured and arranged to make an electrical connection between the lead 403 and the electronic subassembly 452 of the implantable control module 402.

The electrical stimulation system or components of the electrical stimulation system, including the paddle body 444, the one or more of the lead bodies 446, and the implantable control module 402, are typically implanted into the body of a patient. The electrical stimulation system can be used for a variety of applications including, but not limited to deep brain stimulation, neural stimulation, spinal cord stimulation, muscle stimulation, and the like.

The electrodes 434 can be formed using any conductive, biocompatible material. Examples of suitable materials include metals, alloys, conductive polymers, conductive carbon, and the like, as well as combinations thereof. In at least some embodiments, one or more of the electrodes 434 are formed from one or more of: platinum, platinum iridium, palladium, palladium rhodium, or titanium.

Any suitable number of electrodes 434 can be disposed on the lead including, for example, four, five, six, seven, eight, nine, ten, eleven, twelve, fourteen, sixteen, twenty-four, thirty-two, or more electrodes 434. In the case of paddle leads, the electrodes 434 can be disposed on the paddle body 444 in any suitable arrangement. In FIG. 11, the electrodes 434 are arranged into two columns, where each column has eight electrodes 434.

The electrodes of the paddle body 444 (or one or more lead bodies 446) are typically disposed in, or separated by, a non-conductive, biocompatible material such as, for example, silicone, polyurethane, polyetheretherketone ("PEEK"), epoxy, and the like or combinations thereof. The one or more lead bodies 446 and, if applicable, the paddle body 444 may be formed in the desired shape by any process including, for example, molding (including injection molding), casting, and the like. The non-conductive material typically extends from the distal ends of the one or more lead bodies 446 to the proximal end of each of the one or more lead bodies 446.

In the case of paddle leads, the non-conductive material typically extends from the paddle body 444 to the proximal end of each of the one or more lead bodies 446. Additionally, the non-conductive, biocompatible material of the paddle body 444 and the one or more lead bodies 446 may be the same or different. Moreover, the paddle body 444 and the one or more lead bodies 446 may be a unitary structure or can be formed as two separate structures that are permanently or detachably coupled together.

Figure 13A:
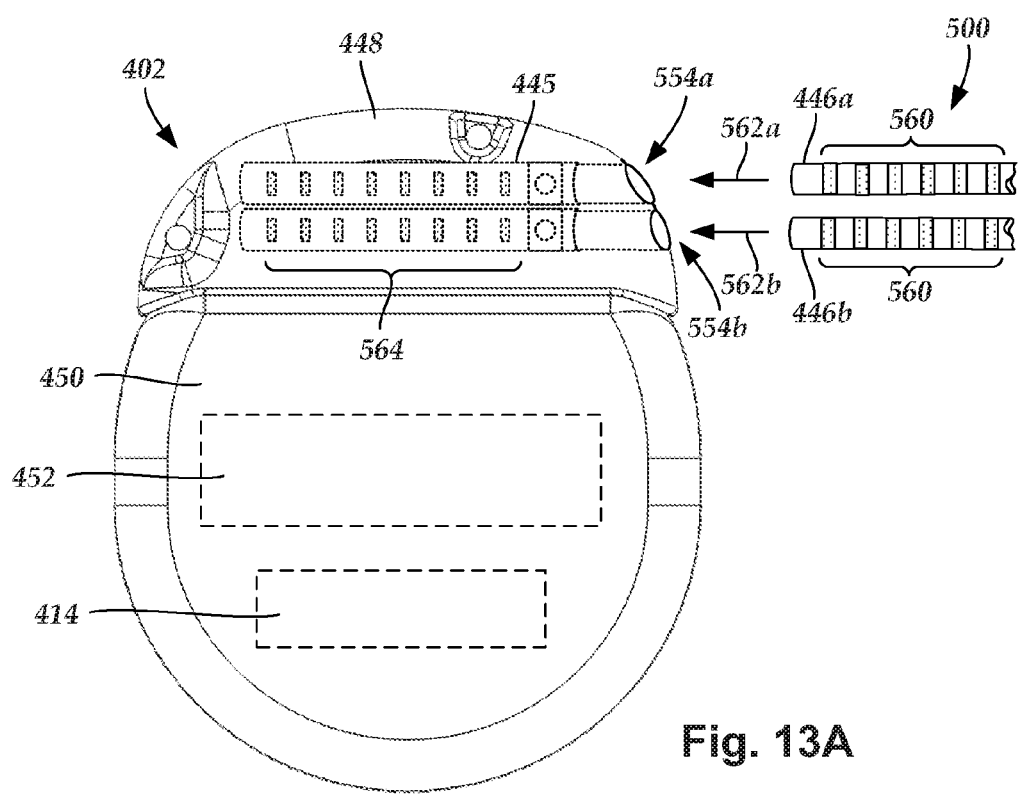
FIG. 13A is a schematic side view of one embodiment of an implantable control module configured and arranged to electrically couple to an elongated device, according to the invention.
Figure 13B:
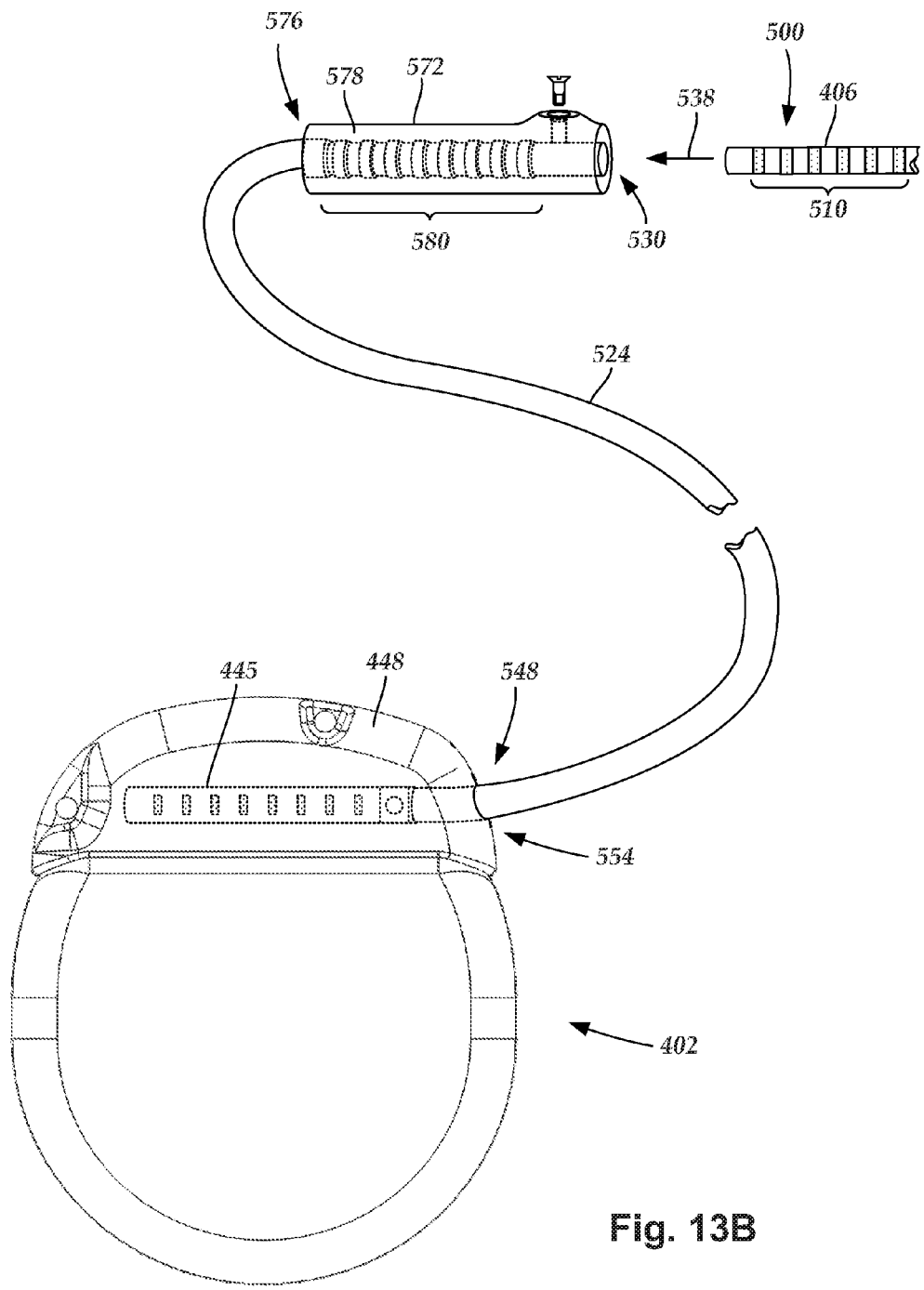
FIG. 13B is a schematic side view of one embodiment of a lead extension configured and arranged to electrically couple an elongated device to an implantable control module, according to the invention.

One or more terminals (e.g., 560 in FIGS. 13A-13B) are typically disposed along the proximal end of the one or more lead bodies 446 of the electrical stimulation system 400 (as well as any splitters, lead extensions, adaptors, or the like) for electrical connection to corresponding connector contacts (e.g., 564 in FIGS. 13A-13B). The connector contacts are disposed in connectors (e.g., 445 in FIGS. 11-13B; and 572 FIG. 13B) which, in turn, are disposed on, for example, the implantable control module 402 (or a lead extension, a splitter, an adaptor, or the like). One or more electrically conductive wires, cables, or the like (i.e., "conductors"—not shown) extend from the terminal(s) to the electrode(s). In at least some embodiments, there is at least one (or exactly one) terminal conductor for each terminal which extends to at least one (or exactly one) of the electrodes.

The one or more conductors are embedded in the non-conductive material of the lead body 446 or can be disposed in one or more lumens (not shown) extending along the lead body 446. For example, any of the conductors may extend distally along the lead body 446 from the terminals 560.

FIG. 13A is a schematic side view of one embodiment of a proximal end of one or more elongated devices 500 configured and arranged for coupling to one embodiment of the connector 445. The one or more elongated devices may include, for example, one or more of the lead bodies 446 of FIG. 11, one or more intermediate devices (e.g., a splitter, the lead extension 524 of FIG. 13B, an adaptor, or the like or combinations thereof), or a combination thereof.

The connector 445 defines at least one port into which a proximal ends 446A, 446B of the elongated device 500 can be inserted, as shown by directional arrows 562a, 562b. In FIG. 13A (and in other figures), the connector housing 448 is shown having two ports 554a, 554b. The connector housing 448 can define any suitable number of ports including, for example, one, two, three, four, five, six, seven, eight, or more ports.

The connector 445 also includes one or more connector contacts, such as connector contact 564, disposed within each port 554a, 554b. When the elongated device 500 is inserted into the ports 554a, 554b, the connector contact(s) 564 can be aligned with the terminal(s) 560 disposed along the proximal end(s) of the elongated device(s) 500 to electrically couple the implantable control module 402 to the electrodes (434 of FIG. 11) disposed on the paddle body 445 of the lead 403. Examples of connectors in implantable control modules are found in, for example, U.S. Pat. Nos. 7,244,150 and 8,224,450, which are incorporated by reference in their entireties.

FIG. 13B is a schematic side view of another embodiment that includes a lead extension 524 that is configured and arranged to couple one or more elongated devices 500 (e.g., one of the lead bodies 446 of FIGS. 11 and 12, the splitter 457 of FIG. 12, an adaptor, another lead extension, or the like or combinations thereof) to the implantable control module 402. In FIG. 13B, the lead extension 524 is shown coupled to a single port 554 defined in the connector 445. Additionally, the lead extension 524 is shown configured and arranged to couple to a single elongated device 500. In alternate embodiments, the lead extension 524 is configured and arranged to couple to multiple ports 554 defined in the connector 445, or to receive multiple elongated devices 500, or both.

A lead extension connector 572 is disposed on the lead extension 524. In FIG. 13B, the lead extension connector 572 is shown disposed at a distal end 576 of the lead extension 524. The lead extension connector 572 includes a connector housing 578. The connector housing 578 defines at least one port 530 into which terminal(s) 560 of the elongated device 500 can be inserted, as shown by directional arrow 538. The connector housing 578 also includes a plurality of connector contacts, such as connector contact 580. When the elongated device 500 is inserted into the port 530, the connector contacts 580 disposed in the connector housing 578 can be aligned with the terminal(s) 560 of the elongated device 500 to electrically couple the lead extension 524 to the electrodes (434 of FIGS. 11 and 12) disposed along the lead (403 in FIGS. 11 and 12).

In at least some embodiments, the proximal end of the lead extension 524 is similarly configured and arranged as a proximal end of the lead 403 (or other elongated device 500). The lead extension 524 may include one or more electrically conductive wires (not shown) that electrically couple the connector contact(s) 580 to a proximal end 548 of the lead extension 524 that is opposite to the distal end 576. The conductive wire(s) disposed in the lead extension 524 can be electrically coupled to one or more terminals (not shown) disposed along the proximal end 548 of the lead extension 524. The proximal end 548 of the lead extension 524 is configured and arranged for insertion into a connector disposed in another lead extension (or another intermediate device). As shown in FIG. 13B, the proximal end 548 of the lead extension 524 is configured and arranged for insertion into the connector 445.

The embodiments of FIGS. 11-13B illustrate a control module 402 with a connector 445 into which a proximal end portion of the lead or lead extension can be removably inserted. It will be recognized, however, that other embodiments of a control module and lead can have the lead or lead extension permanently attached to the control module. Such an arrangement can reduce the size of the control module as the conductors in the lead can be permanently attached to the electronic subassembly. It will also be recognized that, in at least some embodiments, more than one lead can be attached to a control module.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A system for storing stimulation programs or sets of stimulation parameters, the system comprising:
   at least one memory;
   at least one of i) a plurality of stimulation programs or ii) a plurality of sets of stimulation parameters stored on the at least one memory from a plurality of different devices remote from the system and used to stimulate a plurality of different patients;
   at least one processor coupled to the at least one memory and configured and arranged to retrieve the stored stimulation programs or sets of stimulation parameters from the at least one memory when requested and to store additional stimulation programs or sets of stimulation parameters on the at least one memory; and
   a communications arrangement coupled to the at least one processor and configured and arranged to deliver the stored stimulation programs or sets of stimulation parameters to an external device and to receive additional stimulation programs and sets of stimulation parameters from external devices, wherein the system is configured and arranged to permit a user to purchase at least one of the stimulation programs or sets of stimulation parameters and to provide, via the at least one processor and communications arrangement, the purchased at least one of the stimulation programs or sets of stimulation parameters to the user.

2. The system of claim 1, further comprising lead placement information for at least one stimulation therapy stored on the at least one memory and accessible via the at least one processor and communications arrangement.

3. The system of claim 1, wherein the system is configured and arranged, via the at least one processor and communications arrangement, to receive a score or rating for at least one of the stimulation programs or sets of stimulation parameters and to store, on the at least one memory, the score or rating in conjunction with that at least one of the stimulator programs or sets of stimulation parameters.

4. The system of claim 3, wherein the system is configured and arranged, via the at least one processor and communications arrangement, to request the score or rating for at least one of the stimulation programs or sets of stimulation parameters from a user that has received the at least one of the stimulation programs or sets of stimulation parameters.

5. The system of claim 1, wherein the system is configured and arranged, via the at least one processor and communications arrangement, to receive a review or recommendation for at least one of the stimulation programs or sets of stimulation parameters and to store, on the at least one memory, the review or recommendation in conjunction with that at least one of the stimulator programs or sets of stimulation parameters.

6. The system of claim 1, wherein the at least one processor is configured and arranged to analyze the stimulation programs or sets of stimulation parameters and, via at least one machine learning algorithm, generate a new stimulation program or set of stimulation parameters to improve treatment efficacy.

7. The system of claim 1, wherein the at least one processor is configured and arranged to analyze the stimulation programs or sets of stimulation parameters and, via at least one machine learning algorithm, generate a modified stimulation program or set of stimulation parameters to improve treatment efficacy.

8. The system of claim 1, wherein the at least one processor is configured and arranged to analyze the stimulation programs or sets of stimulation parameters and, via at least one machine learning algorithm, generate a new stimulation program or set of stimulation parameters based on at least one of a patient characteristic; disease or disorder or condition; symptom or symptoms; stimulation device or lead type; or electrode or lead location.

9. A computer-based method, wherein a plurality of actions are performed by a processor, the actions comprising:

receiving a plurality of stimulation programs or a plurality of sets of stimulation parameters from a plurality of different devices remote from the processor and used to stimulate a plurality of different patients;

storing the plurality of stimulation programs or plurality of sets of stimulation parameters on at least one memory;

retrieving the stored stimulation programs or sets of stimulation parameters from the at least one memory when requested by user; and permitting a user to purchase at least one of the stimulation programs or sets of stimulation parameters and providing the purchased at least one of the stimulation programs or sets of stimulation parameters to the user.

10. The computer-based method of claim 9, wherein the actions further comprise receiving a score or rating for at least one of the stimulation programs or sets of stimulation parameters and storing, on the at least one memory, the score or rating in conjunction with that at least one of the stimulator programs or sets of stimulation parameters.

11. The computer-based method of claim 10, wherein the actions further comprise requesting the score or rating for at least one of the stimulation programs or sets of stimulation parameters from a user that has received the at least one of the stimulation programs or sets of stimulation parameters.

12. The computer-based method of claim 9, wherein the actions further comprise receiving a review or recommendation for at least one of the stimulation programs or sets of stimulation parameters and storing, on the at least one memory, the score or rating in conjunction with that at least one of the stimulator programs or sets of stimulation parameters.

13. The computer-based method of claim 9, wherein the actions further comprise analyzing the stimulation programs or sets of stimulation parameters and, via at least one machine learning algorithm, generating a new stimulation program or set of stimulation parameters to improve treatment efficacy.

14. The computer-based method of claim 9, wherein the actions further comprise analyzing the stimulation programs or sets of stimulation parameters and, via at least one machine learning algorithm, generating a modified stimulation program or set of stimulation parameters to improve treatment efficacy.

15. The computer-based method of claim 9, wherein the actions further comprise analyzing the stimulation programs or sets of stimulation parameters and, via at least one machine learning algorithm, generating a new stimulation program or set of stimulation parameters based on at least one of a patient characteristic; disease or disorder or condition; symptom or symptoms; stimulation device or lead type; or electrode or lead location.

16. The computer-based method of claim 9, wherein the actions further comprise categorizing the stimulation programs or sets of stimulation parameters and to permit the user to access the stimulation programs or sets of stimulation parameters via the categorization.

17. The system of claim 1, wherein the system is configured and arranged to categorize the stimulation programs or sets of stimulation parameters and to permit the user to access the stimulation programs or sets of stimulation parameters via the categorization.

* * * * *